(12) United States Patent
Chen et al.

(10) Patent No.: US 10,390,718 B2
(45) Date of Patent: *Aug. 27, 2019

(54) MULTI-SPECTRAL PHYSIOLOGIC VISUALIZATION (MSPV) USING LASER IMAGING METHODS AND SYSTEMS FOR BLOOD FLOW AND PERFUSION IMAGING AND QUANTIFICATION IN AN ENDOSCOPIC DESIGN

(71) Applicant: East Carolina University, Greenville, NC (US)

(72) Inventors: Cheng Chen, Greenville, NC (US); T. Bruce Ferguson, Jr., Raleigh, NC (US); Kenneth Michael Jacobs, Greenville, NC (US)

(73) Assignee: East Carolina University, Greenville, NC (US)

( * ) Notice: Subject to any disclaimer, the term of this patent is extended or adjusted under 35 U.S.C. 154(b) by 38 days.

This patent is subject to a terminal disclaimer.

(21) Appl. No.: 15/688,472

(22) Filed: Aug. 28, 2017

(65) Prior Publication Data
US 2018/0020932 A1    Jan. 25, 2018

Related U.S. Application Data

(63) Continuation-in-part of application No. 15/054,830, filed on Feb. 26, 2016, now Pat. No. 10,058,256.
(Continued)

(51) Int. Cl.
*A61B 5/02* (2006.01)
*A61B 5/026* (2006.01)
(Continued)

(52) U.S. Cl.
CPC ............ *A61B 5/0261* (2013.01); *A61B 1/005* (2013.01); *A61B 1/00009* (2013.01); *A61B 1/04* (2013.01);
(Continued)

(58) Field of Classification Search
CPC ..... A61B 5/0261; A61B 5/0077; A61B 5/721; A61B 5/7278; A61B 1/3132;
(Continued)

(56) References Cited

U.S. PATENT DOCUMENTS

| | | |
|---|---|---|
| 4,541,433 A | 9/1985 | Baudino |
| 5,058,596 A | 10/1991 | Makino et al. |

(Continued)

FOREIGN PATENT DOCUMENTS

| | | |
|---|---|---|
| EP | 2 524 650 A2 | 11/2012 |
| JP | 10-290791 | 11/1998 |

(Continued)

OTHER PUBLICATIONS

U.S. Appl. No. 15/559,605, filed Sep. 19, 2017, Peng et al.
(Continued)

*Primary Examiner* — Christopher Koharski
*Assistant Examiner* — Natasha Patel
(74) *Attorney, Agent, or Firm* — Stanek Lemon Crouse & Meeks, PA

(57) ABSTRACT

Multispectral imaging systems are provided including a first light source having a first wavelength configured to image a sample; a second light source, different from the first light source, having a second wavelength, different from the first wavelength, configured to image the sample; and at least a third light source, different from the first and second light sources, having a third wavelength, different from the first and second wavelengths, configured to image the sample. A camera is configured to receive information related to the first, second and at least third light sources from the sample. A processor is configured to combine the information related to the first, second and at least third light sources provided by the camera to image an anatomical structure of the sample, image physiology of blood flow and perfusion of the
(Continued)

sample and/or synthesize the anatomical structure and the physiology of blood flow and perfusion of the sample in terms of a blood flow rate distribution. The imaging system is directed and focused on a field of view (FOV) in a region of interest of the sample using an endoscope.

20 Claims, 28 Drawing Sheets

Related U.S. Application Data

(60) Provisional application No. 62/136,010, filed on Mar. 20, 2015.

(51) Int. Cl.
  *A61B 1/04* (2006.01)
  *A61B 1/06* (2006.01)
  *A61B 1/00* (2006.01)
  *A61B 1/005* (2006.01)
  *A61B 5/00* (2006.01)
  *A61B 1/313* (2006.01)

(52) U.S. Cl.
  CPC .......... *A61B 1/0638* (2013.01); *A61B 1/3132* (2013.01); *A61B 5/0077* (2013.01); *A61B 5/721* (2013.01); *A61B 5/7278* (2013.01); *A61B 2576/00* (2013.01)

(58) Field of Classification Search
  CPC ..... A61B 1/00009; A61B 1/0638; A61B 1/04; A61B 1/005; A61B 2576/00
  See application file for complete search history.

(56) References Cited

U.S. PATENT DOCUMENTS

| | | |
|---|---|---|
| 5,074,307 A | 12/1991 | Aizu et al. |
| 5,129,400 A | 7/1992 | Makino et al. |
| 5,161,531 A | 11/1992 | Parsons et al. |
| 5,240,006 A | 8/1993 | Fujii et al. |
| 5,291,885 A | 3/1994 | Taniji et al. |
| 5,291,886 A | 3/1994 | Katayama et al. |
| 5,490,505 A | 2/1996 | Diab et al. |
| 5,588,436 A | 12/1996 | Narayanan et al. |
| 5,692,510 A | 12/1997 | Gordon et al. |
| 5,860,922 A | 1/1999 | Gordon et al. |
| 6,045,511 A | 4/2000 | Ott et al. |
| 6,263,227 B1 | 7/2001 | Boggett et al. |
| 6,323,880 B1 | 11/2001 | Yamada |
| 6,537,223 B1 | 3/2003 | Kristiansen |
| 6,587,701 B1 | 7/2003 | Stranc et al. |
| 6,631,286 B2 | 10/2003 | Pfeiffer et al. |
| 6,671,540 B1 | 12/2003 | Hochman |
| 6,766,188 B2 | 7/2004 | Soller |
| 6,915,154 B1 | 7/2005 | Docherty et al. |
| 6,944,494 B2 | 9/2005 | Forrester et al. |
| 6,974,416 B2 | 12/2005 | Booker et al. |
| 7,031,504 B1 | 4/2006 | Argiro et al. |
| 7,096,058 B2 | 8/2006 | Miyahara et al. |
| 7,113,817 B1 | 9/2006 | Winchester, Jr. et al. |
| 7,200,431 B2 | 4/2007 | Franco et al. |
| 7,231,243 B2 | 6/2007 | Tearney et al. |
| 7,270,637 B2 | 9/2007 | Shin |
| 7,309,313 B2 | 12/2007 | Nakata et al. |
| 7,404,640 B2 | 7/2008 | Ferguson et al. |
| 7,468,039 B2 | 12/2008 | Lui |
| 7,496,395 B2 | 2/2009 | Serov et al. |
| 7,541,602 B2 | 6/2009 | Metzger et al. |
| 7,542,790 B2 | 6/2009 | Jensen et al. |
| 7,809,225 B2 | 10/2010 | Bouma et al. |
| 7,809,226 B2 | 10/2010 | Bouma et al. |
| 9,226,673 B2 | 1/2016 | Ferguson, Jr. et al. |
| 9,271,658 B2 | 3/2016 | Ferguson, Jr. et al. |

| | | |
|---|---|---|
| 2001/0035503 A1 | 11/2001 | Quistorff et al. |
| 2002/0016533 A1 | 2/2002 | Marchitto et al. |
| 2002/0173723 A1 | 11/2002 | Lewis et al. |
| 2003/0225328 A1 | 12/2003 | DeMeester et al. |
| 2003/0231511 A1 | 12/2003 | Thibault |
| 2004/0068164 A1 | 4/2004 | Diab et al. |
| 2005/0046969 A1 | 3/2005 | Beatson et al. |
| 2006/0058662 A1 | 3/2006 | Kobayashi et al. |
| 2006/0241460 A1 | 10/2006 | Kimura et al. |
| 2006/0291708 A1 | 12/2006 | Dehmeshki et al. |
| 2007/0008615 A1 | 1/2007 | Miyawaki et al. |
| 2007/0109784 A1 | 5/2007 | Kosnick et al. |
| 2007/0203413 A1 | 8/2007 | Frangioni |
| 2008/0049268 A1 | 2/2008 | Hardy et al. |
| 2008/0071176 A1 | 3/2008 | Docherty et al. |
| 2008/0107361 A1 | 5/2008 | Asukai et al. |
| 2008/0132794 A1 | 6/2008 | Alfano et al. |
| 2008/0188726 A1 | 8/2008 | Presura et al. |
| 2008/0262359 A1 | 10/2008 | Tearney et al. |
| 2009/0041201 A1 | 2/2009 | Wang et al. |
| 2009/0054908 A1* | 2/2009 | Zand .................. A61B 5/0071 606/130 |
| 2009/0118623 A1 | 5/2009 | Serov et al. |
| 2009/0177098 A1 | 7/2009 | Yakubo et al. |
| 2009/0209834 A1 | 8/2009 | Fine |
| 2009/0214098 A1 | 8/2009 | Hornegger et al. |
| 2009/0216098 A1 | 8/2009 | Stranc et al. |
| 2010/0056936 A1 | 3/2010 | Fujii et al. |
| 2010/0067767 A1 | 3/2010 | Arakita et al. |
| 2010/0069759 A1 | 3/2010 | Schuhrke et al. |
| 2010/0168585 A1 | 7/2010 | Fujii et al. |
| 2010/0172567 A1 | 7/2010 | Prokoski |
| 2010/0209002 A1 | 8/2010 | Thiel et al. |
| 2010/0284693 A1 | 11/2010 | Agmon et al. |
| 2010/0305454 A1 | 12/2010 | Dvorsky et al. |
| 2011/0013002 A1 | 1/2011 | Thompson et al. |
| 2011/0068007 A1 | 3/2011 | Pang et al. |
| 2011/0071382 A1 | 3/2011 | Miyazaki et al. |
| 2011/0137169 A1 | 6/2011 | Akaki et al. |
| 2011/0164035 A1 | 7/2011 | Liao et al. |
| 2011/0169978 A1 | 7/2011 | Lasser et al. |
| 2011/0176048 A1 | 7/2011 | Rockley |
| 2011/0319775 A1 | 12/2011 | Fujii et al. |
| 2012/0071769 A1 | 3/2012 | Dunn et al. |
| 2012/0078113 A1 | 3/2012 | Hitestone et al. |
| 2012/0095354 A1 | 4/2012 | Dunn et al. |
| 2012/0108956 A1 | 5/2012 | Warger, II et al. |
| 2012/0165627 A1 | 6/2012 | Yamamoto |
| 2012/0191005 A1 | 7/2012 | Sobol et al. |
| 2012/0277559 A1 | 11/2012 | Kohl-Bareis et al. |
| 2013/0324866 A1* | 12/2013 | Gladshtein ........... A61B 5/0059 600/507 |
| 2013/0345560 A1 | 12/2013 | Ferguson, Jr. et al. |
| 2014/0003740 A1 | 1/2014 | Bone |
| 2014/0161421 A1 | 6/2014 | Shoemaker et al. |
| 2014/0187966 A1 | 7/2014 | Theirman |
| 2014/0276097 A1 | 9/2014 | Sharonov |
| 2014/0285702 A1 | 9/2014 | Hagashiyama et al. |
| 2014/0293091 A1 | 10/2014 | Rhoads et al. |
| 2014/0340482 A1 | 11/2014 | Kanarowski |
| 2015/0077716 A1 | 3/2015 | Peng |
| 2015/0342479 A1 | 12/2015 | Liu et al. |
| 2016/0198961 A1 | 7/2016 | Homyk et al. |
| 2016/0317041 A1 | 11/2016 | Porges et al. |
| 2016/0358332 A1 | 12/2016 | Watanabe |
| 2017/0049377 A1 | 2/2017 | Littell |
| 2017/0091962 A1 | 3/2017 | Hagiwara |
| 2017/0135555 A1 | 5/2017 | Yoshizaki |
| 2017/0270379 A1 | 9/2017 | Kasai et al. |
| 2018/0153422 A1 | 6/2018 | Watanabe |

FOREIGN PATENT DOCUMENTS

| | | |
|---|---|---|
| JP | 2005-118325 | 5/2005 |
| JP | 2008-139543 | 6/2008 |
| JP | 2012-130629 | 7/2012 |
| JP | 2015-223463 | 12/2015 |
| WO | 97/43950 | 11/1997 |
| WO | 98/44839 | 10/1998 |

(56) References Cited

FOREIGN PATENT DOCUMENTS

| | | |
|---|---|---|
| WO | WO 2006/021096 A1 | 3/2006 |
| WO | WO 2006/116672 A2 | 11/2006 |
| WO | WO 2009/127972 A2 | 10/2009 |
| WO | WO 2010/131550 A1 | 11/2010 |
| WO | WO 2012/096878 A2 | 7/2012 |
| WO | WO 2013/190391 A2 | 12/2013 |
| WO | WO 2014/006465 A1 | 1/2014 |
| WO | WO 2014/009859 A2 | 1/2014 |
| WO | WO 2016/061041 A1 | 4/2016 |
| WO | WO 2016/061052 A1 | 4/2016 |

OTHER PUBLICATIONS

U.S. Appl. No. 15/559,646, filed Sep. 19, 2017, Peng et al.
Furstenberg et al. "Laser speckle reduction techniques for mid-infrared microscopy and stand-off spectroscopy" *Proceedings of SPIE* 10210:1021004-1-8 (2017).
Zhang et al. "Multimodal imaging of ischemic wounds" *Proceedings of SPIE* 8553:85531G-1-8 (2012).
U.S. Appl. No. 15/518,545, filed Apr. 12, 2017, Chen et al.
U.S. Appl. No. 15/518,548, filed Apr. 12, 2017, Chen et al.
Aizu, Y et al. (1991) "Bio-Speckle Phenomena and Their Application to the Evaluation of *Blood Flow*" Optics and Laser Technology, vol. 23, No. 4, Aug. 1, 1991.
Brezinski, M. E., G. J. Tearney, et al. (1996). "Imaging of *coronary artery* microstructure (in vitro) with optical coherence tomography." American Journal of Cardiology 77 (1): 92-93.
Briers et al., (1995) "Quasi real-time digital version of single-exposure speckle photography for full-field monitoring of velocity or flow fields," Optics Communications 116: 36-42.
Briers, J. David, (2001) "Laser Doppler, speckle and related techniques for blood perfusion mapping and imaging," Physiol. Meas. 22: R35-R66.
Chen, Z. P., T. E. Milner, et al. (1997). "Noninvasive imaging of in vivo *blood flow* velocity using optical Doppler tomography." Optics Letters 22(14): 1119-1121.
Cheng et al., (2004) "Laser speckle imaging of blood flow in microcirculation," Phys. Med. Biol., 49: 1347-1357.
Choi et al., "Linear response range characterization and in vivo application of laser speckle imaging of blood flow dynamics," Journal of Biomedical Optics, Jul./Aug. 2006, 11(4): 041129.
Cioffi, G. A. (2001). "Three common assumptions about ocular *blood flow* and glaucoma." Survey of Ophthalmology 45: S325-S331.
Draijer, Matthijs J., "High Speed Perfusion Imaging Based on Laser Speckle Fluctuations," Printed by Ridderprint, Ridderkerk, The Netherlands 2010, 145 pages.
Draijer et al., "Twente Optical Perfusion Camera: system overview and performance for video rate laser Doppler perfusion imaging," Optics Express, Mar. 2, 2009, 17(5): 3211-3225.
Duncan et al., "Can laser speckle flowmetry be made a quantitative tool?," J. Opt. Soc. Am. A, Aug. 2008, 24(8): 2088-2094.
Dunn et al. "Dynamic imaging of cerebral blood flow using laser *speckle*", J. of Cerebral Blood Flow and Metabolism 21, 195-201 (2001).
Dunn et al., (2011) A Transmissive Laser Speckle Imaging Technique for Measuring Deep Tissue Blood Flow: An Example Application in Finger Joints, Lasers in Surgery and Medicine, 43: 21-28.
Eun, H. C. (1995). "Evaluation of skin *blood flow* by laser Doppler flowmetry. [Review] [151 refs]." Clinics in Dermatology 13(4): 337-47.
Fercher et al., "Flow Visualization by Means of Single-Exposure Speckle Photography," Optics Communications, Jun. 1, 1981, 37(5): 326-330.
Gandjbakhche, A. H., P. Mills, et al. (1994). "Light-Scattering Technique for the Study of Orientation and Deformation of Red-Blood-Cells in a Concentrated Suspension." Applied Optics 33(6): 1070-1078.

International Search Report and the Written Opinion of the International Searching Authority, or the Declaration, PCT/US2016/020201, dated Jul. 27, 2016, 12 pages.
Izatt, J. A., M. D. Kulkarni, et al. (1996). "Optical coherence tomography and microscopy in gastrointestinal tissues." IEEE Journal of Selected Topics in Quantum Electronics 2(4): 1017.
Jang, I. K., G. J. Tearney, et al. (2001). "Visualization of Tissue Prolapse Between Coronary Stent Struts by Optical Coherence Tomography: Comparison With Intravascular Ultrasound." Images in Cardiovascular Medicine, American Heart Association, http://circ.ahajournals.org/content, p. 2754.
Konishi and Fujii "Real-time visualization of retinal microcirculation by laser flowgraphy", Opt. Eng. 34, 753-757 (1995).
Kruijt et al., (2006), "Laser speckle imaging of dynamic changes in flow during photodynamic therapy," Lasers Med Sci, 21: 208-212.
Leitgeb, R. A., L. Schmetterer, et al. (2003). "Real-time assessment of retinal *blood flow* with ultrafast acquisition by color Doppler Fourier domain optical coherence tomography." Optics Express 11(23): 3116-3121.
Lesnick et al., "New Generation Optical Would Monitoring Device," CW Optics, Inc., Yorktown, Virginia, USA, Admitted Prior Art, 1 page.
Li et al., "Imaging cerebral blood flow through the intact rate skull with temporal laser speckle imaging," Optics Letters, Jun. 15, 2006, 31(12): 1824-1826.
Matsievskii, D.D., (2004) "Blood Flow Measurements in Studies of Macro- and Microcirculation," Bulletin of Experimental Biology and Medicine, 6: 541-544.
Nadkarni, Seemantini K. et al (2005) "Characterization of Atherosclerotic Plaques by Laser *Speckle Imaging*" Circulation vol. 112, pp. 885-892.
Nelson, J. S., K. M. Kelly, et al. (2001). "Imaging *blood flow* in human port-wine stain in situ and in real time using optical Doppler tomography." Archives of Dermatology 137(6): 741-744.
Ohtsubo et al., (1976) "Velocity measurement of a diffuse object by using time-varying speckles," Optical and Quantum Electronics, 8: 523-529.
Oshima, M., R. Torii, et al. (2001). "Finite element simulation of *blood flow* in the cerebral artery." Computer Methods in Applied Mechanics and Engineering 191 (6-7): 661-671.
Parthasarathy et al., "Laser speckle contrast imaging of cerebral blood flow in humans during neurosurgery: a pilot clinical study," Journal of Biomedical Optics, 15(6) Nov./Dec. 2010, pp. 066030-1 to 066030-8.
Rege et al., "Multiexposure laser speckle contrast imaging of the angiogenic microenvironment," Journal of Biomedical Optics, 16(5), May 2011, pp. 056006-1 to 056006-10.
Ren, Hongwu et al., "Phase-Resolved Functional Optical Coherence Tomography: Simultaneous Imaging of In Situ Tissue Structure, *Blood Flow* Velocity, Standard Deviation, Birefringence, and Stokes Vectors in Human Skin," Optics Letters, vol. 27, No. 19, Oct. 1, 2002, pp. 1702-1704.
Richards G.J. et al. (1997) "Laser Speckle Contrast Analysis (LASCA): A Technique for Measuring Capillary *Blood Flow* Using the First Order Statistics of Laser Speckle Patterns" Apr. 2, 1997.
Ruth, B. "*blood flow* determination by the laser speckle method", Int J Microcirc: Clin Exp, 1990, 9:21-45.
Ruth, et al., (1993) "Noncontact Determination of Skin Blood Flow Using the Laser Speckle Method: Application to Patients with Peripheral Arterial Occlusive Disease (PAOD) and to Type-I Diabetes," Lasers in Surgery and Medicine 13: 179-188.
Subhash, Hrebesh M., "Biophotonics Modalities for High-Resolution Imaging of Microcirculatory Tissue Beds Using Endogenous Contrast: A Review of Present Scenario and Prospects," International Journal of Optics, vol. 2011, Article ID 293684, 20 pages.
Tearney et al., "Atherosclerotic plaque characterization by spatial and temporal speckle pattern analysis", CLEO 2001, vol. 56, pp. 307-307.
Wang, X. J., T. E. Milner, et al. (1997). "Measurement of fluid-flow-velocity profile in turbid media by the use of optical Doppler tomography." Applied Optics 36(1): 144-149.

(56) References Cited

OTHER PUBLICATIONS

Wardell et al., "ECG-Triggering of the Laser Doppler Perfusion Imaging Signal," Proceedings of the 20$^{th}$ Annual International Conference of the IEEE Engineering in Medicine and Biology Socieity, vol. 20, No. 4, 1998, pp. 1879-1880.

Weber et al., (2004) "Optical imaging of the spatiotemporal dynamics of cerebral blood flow and oxidative metabolism in the rat barrel cortex," European Journal of Neuroscience, 20: 2664-2670.

White, Brian R. et al., "In Vivo Dynamic Human Retinal *Blood Flow* Imaging Using Ultra-High-Speed Spectral Domain Optical Doppler Tomography," Optics Express, Dec. 15, 2003, 11(25): 3490-3497.

Wussling et al., "Laser diffraction and speckling studies in skeletal and heart muscle", Biomed, Biochem, Acta, 1986, 45(1/2):S 23-S 27.

Yazdanfar et al., "In Vivo imaging in *blood flow* in human retinal vessels using color Doppler optical coherence tomography", SPIE, 1999 vol. 3598, pp. 177-184.

Yazdanfar, S., A. M. Rollins, et al. (2000). "Imaging and velocimetry of human retinal circulation with color Doppler optical coherence tomography." Optics Letters, vol. 25, No. 19, Oct. 1, 2000, pp. 1448-1450.

Yazdanfar, S., A. M. Rollins, et al. (2003). "In vivo imaging of human retinal flow dynamics by color Doppler optical coherence tomography." Archives of Ophthalmology 121(2): 235-239.

Zakharov et al., "Dynamic laser speckle imaging of cerebral blood flow," Optics Express, vol. 17, No. 16, Aug. 3, 2009, pp. 13904-13917.

Zakharov et al., "Quantitative modeling of laser speckle imaging," Optics Letters, Dec. 1, 2006; 31(23): 3465-3467.

Zhao, Y. H., Z. P. Chen, et al. (2000). "Doppler standard deviation imaging for clinical monitoring of in vivo human skin *blood flow*." Optics Letters 25(18): 1358-1360.

International Search Report corresponding to International Patent Application No. PCT/US2018/045715 (14 pages) (dated Dec. 11, 2018).

Redding et al. "Speckle-free laser imaging using random laser illumination" *Nature Photonics* 6:355-359 (2012).

Ren et al. "A simultaneous multimodal imaging system for tissue functional parameters" *Proceedings of SPIE* 8937:893706-1-12 (2014).

European Search Report corresponding to European Patent Application No. 16769288.8 (4 pages) (dated Oct. 11, 2018).

Gioux et al., "Motion-gated acquisition for in vivo optical imaging," Journal of Biomedical Optics, Nov./Dec. 2009, vol. 14(6), pp. 064038-1 through 064038-8.

\* cited by examiner

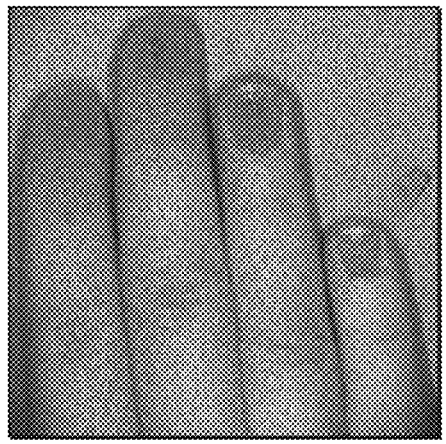 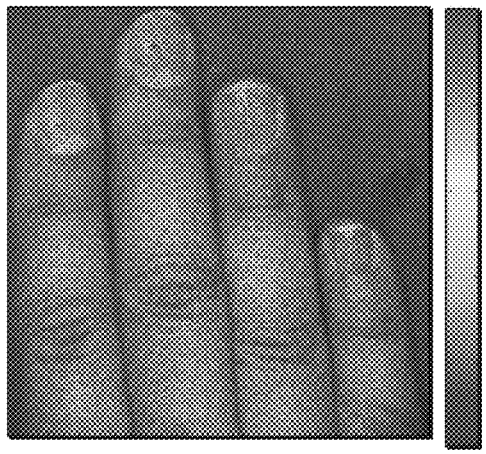
FIG. 7A    FIG. 7B
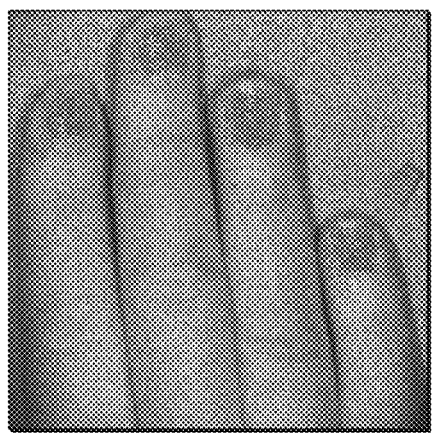 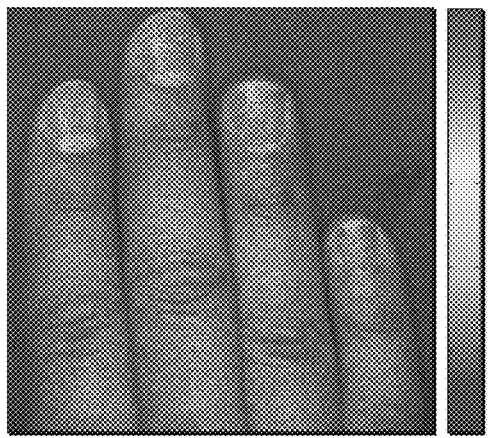
FIG. 8A    FIG. 8B

PANEL A

PANEL B

PANEL C

PANEL D (A+B+C)

HIGH FLOW
MEDIUM FLOW
LOW FLOW

PANEL A

PANEL B

PANEL C

PANEL D

PANEL A

PANEL B

PANEL C

PANEL D

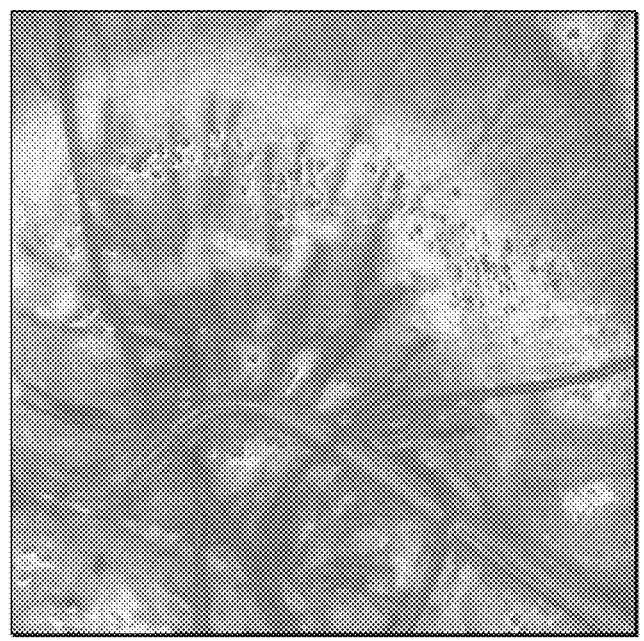
FIG. 14E
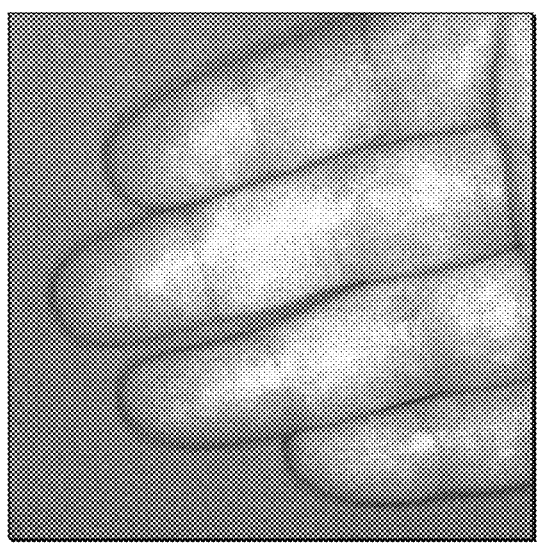
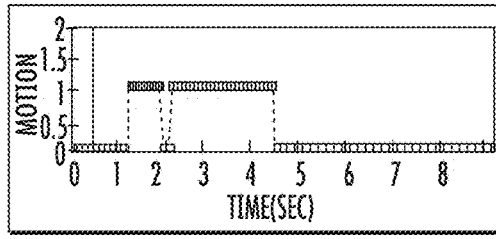
FIG. 15A
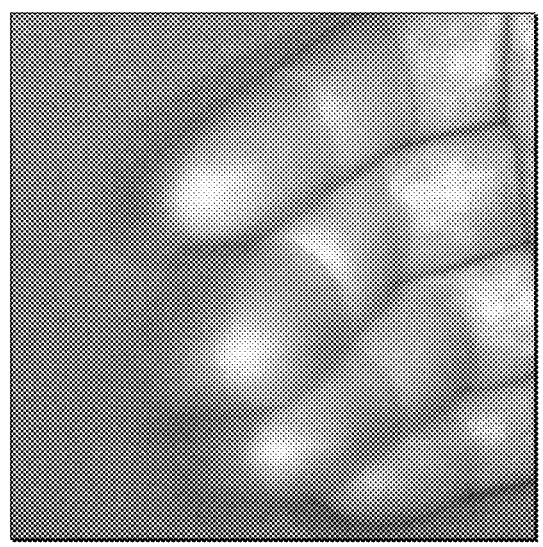
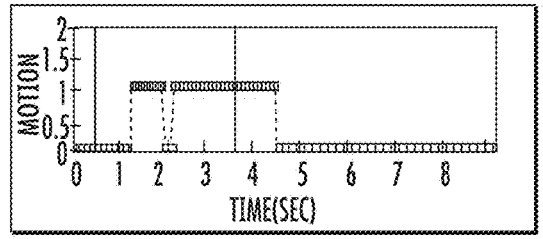
FIG. 15B

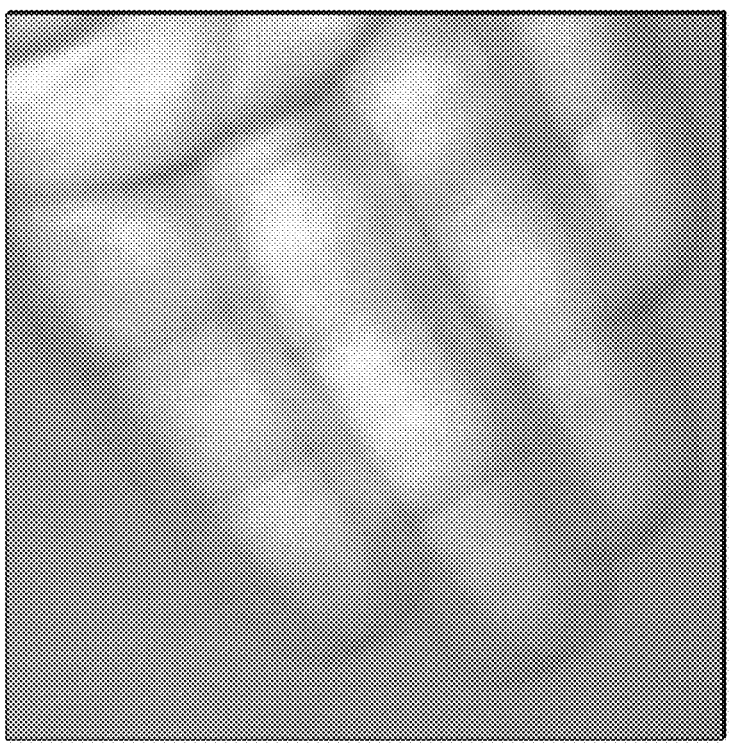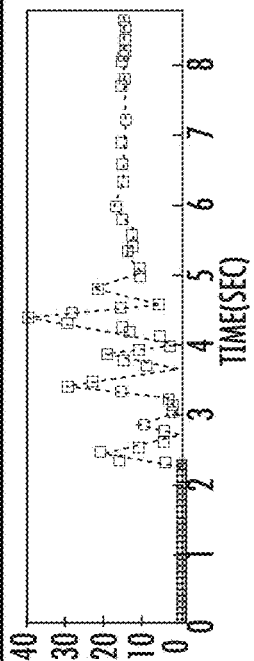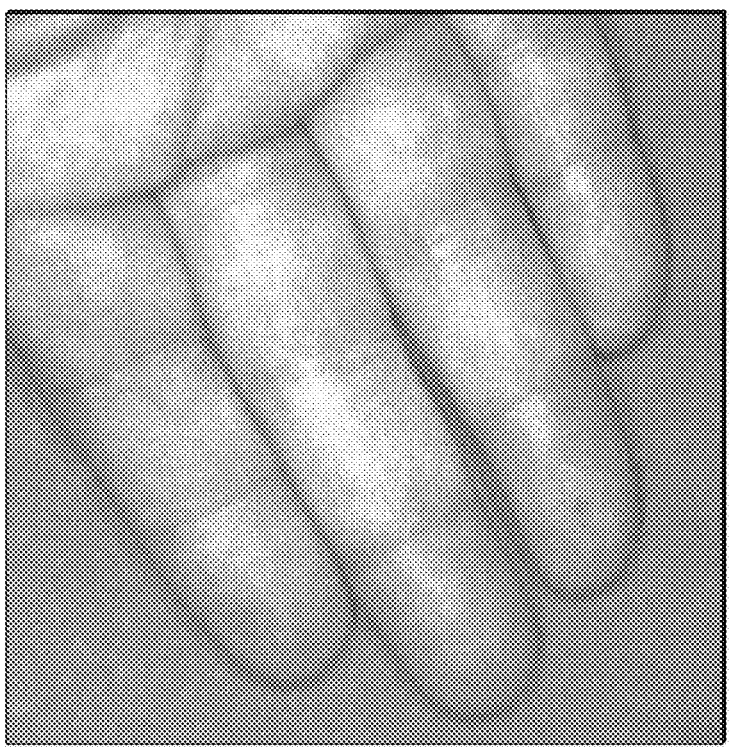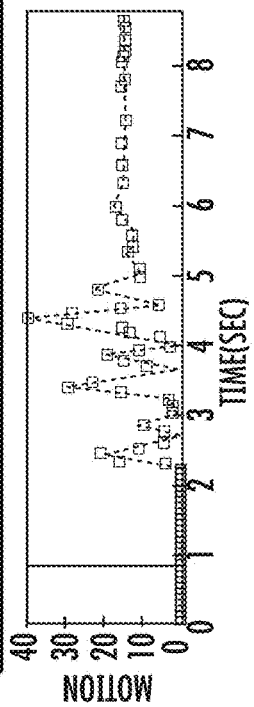
FIG. 16A
FIG. 16B

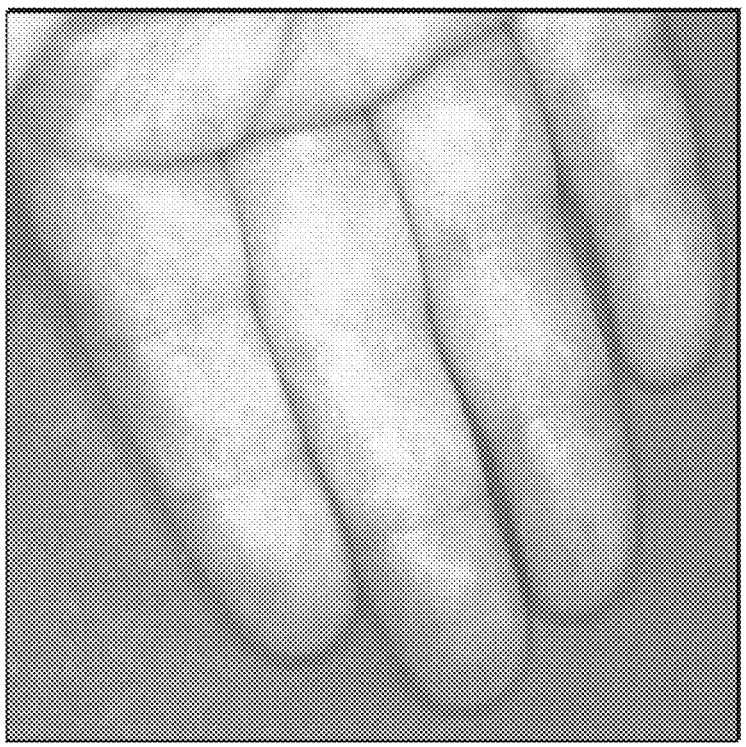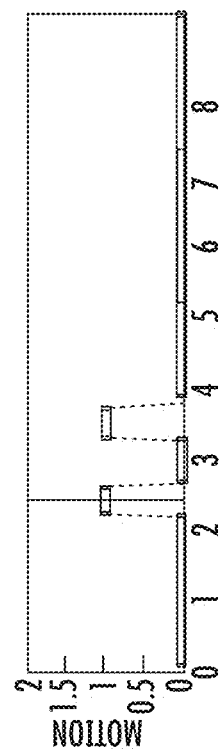
FIG. 18B
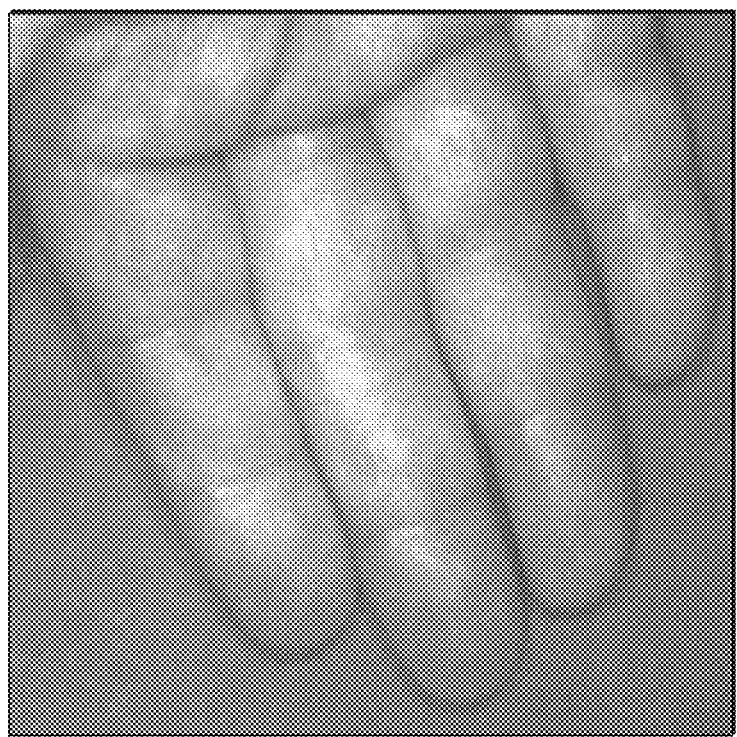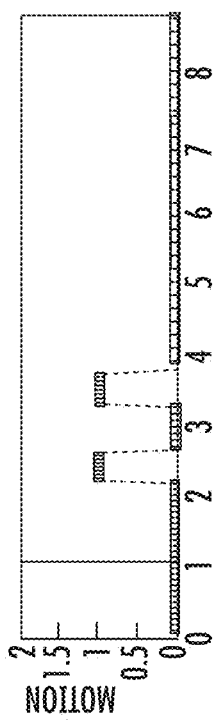
FIG. 18A

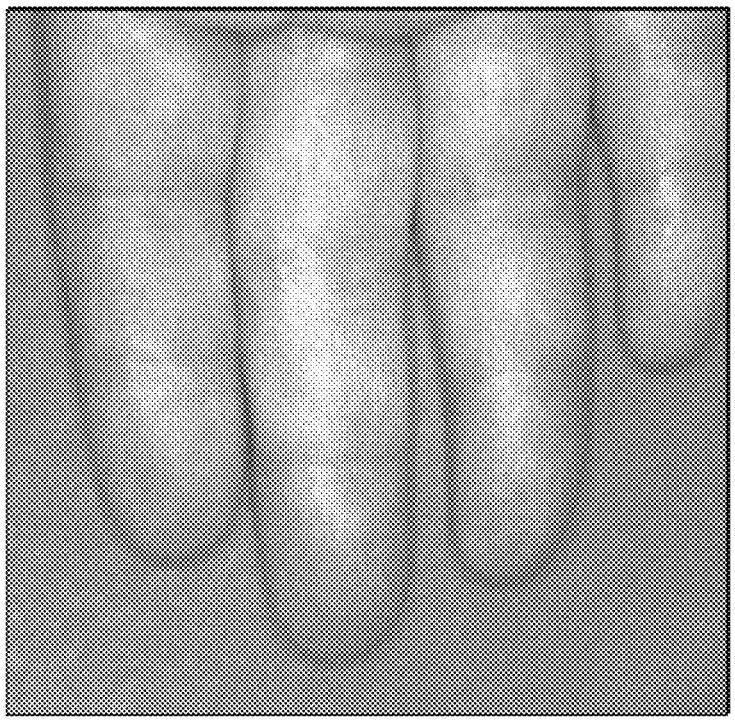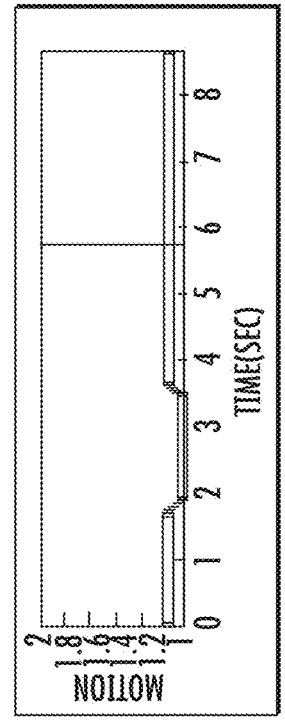
FIG. 19B
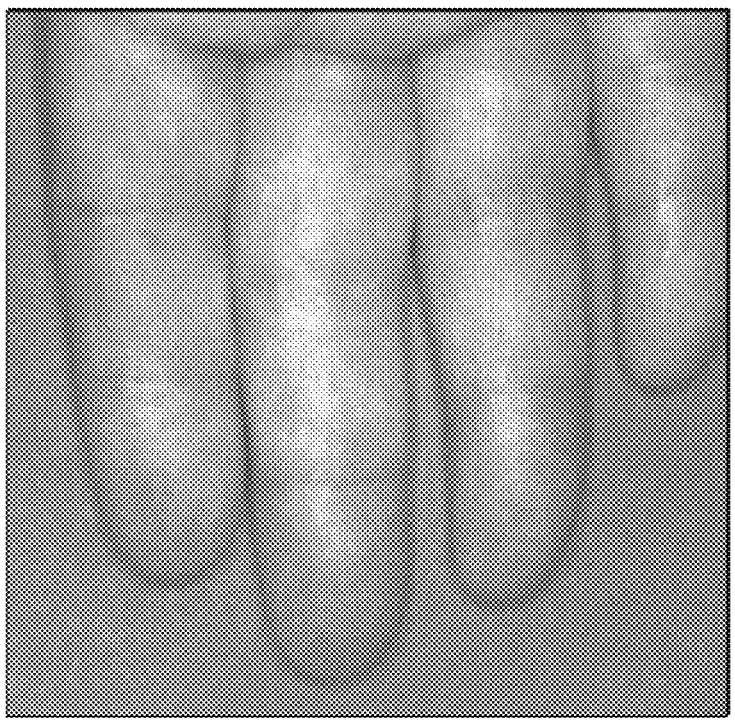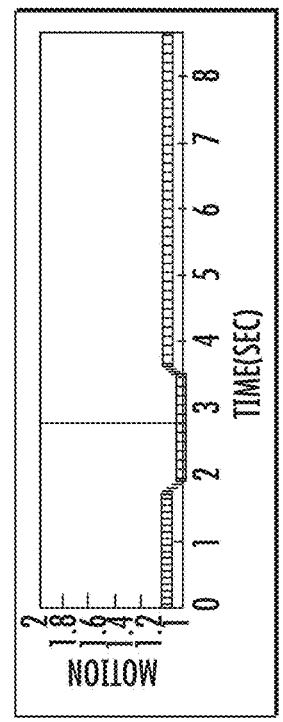
FIG. 19A

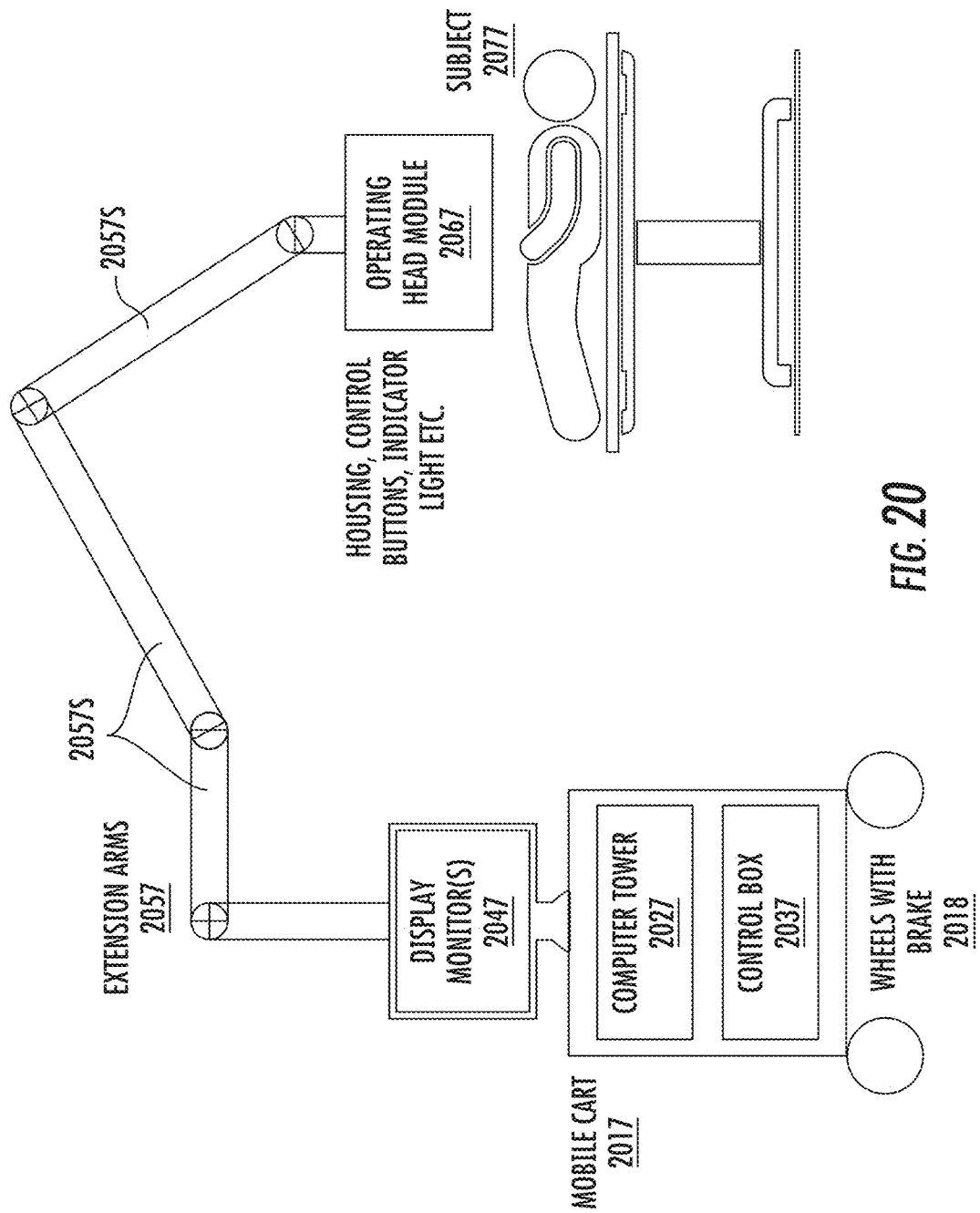

TIME MARK (SECONDS) AND IMAGE QUALITY (COLOR) BAR
GREEN: GOOD IMAGE QUALITY
YELLOW: MEDIUM IMAGE QUALITY
RED: POOR IMAGE QUAILTY

TIME MARK (SECONDS) AND IMAGE QUALITY (COLOR) BAR
GREEN: GOOD IMAGE QUALITY
YELLOW: MEDIUM IMAGE QUALITY
RED: POOR IMAGE QUAILTY

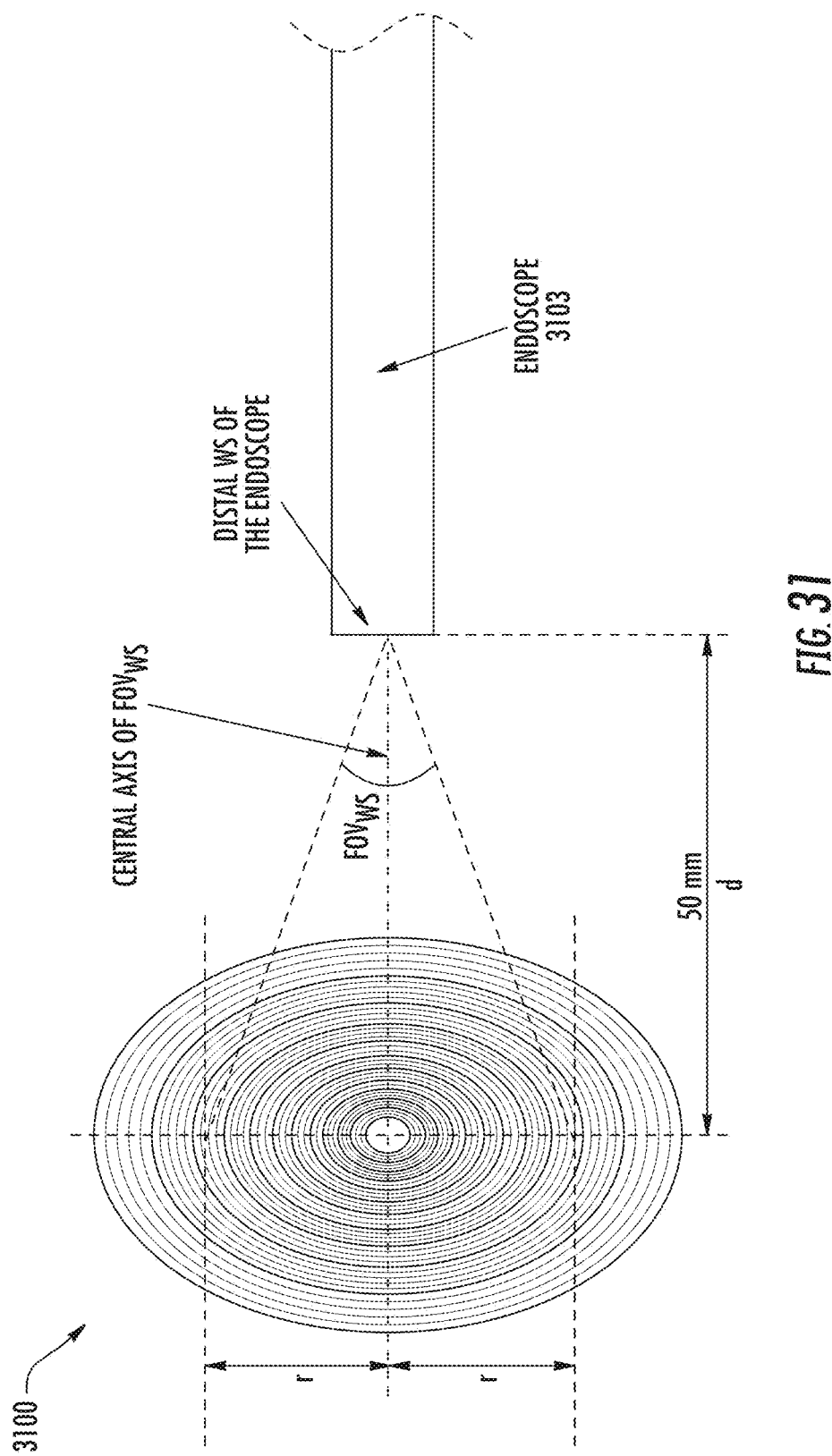

MULTI-SPECTRAL PHYSIOLOGIC VISUALIZATION (MSPV) USING LASER IMAGING METHODS AND SYSTEMS FOR BLOOD FLOW AND PERFUSION IMAGING AND QUANTIFICATION IN AN ENDOSCOPIC DESIGN

CLAIM OF PRIORITY

The present application is a continuation-in-part of U.S. patent application Ser. No. 15/054,830, filed Feb. 26, 2016, which claims the benefit of and priority to U.S. Provisional Application No. 62/136,010, filed Mar. 20, 2015, entitled Multi-Spectral Laser Imaging (MSLI) Methods and Systems for Blood Flow and Perfusion Imaging and Quantification, the disclosures of which are hereby incorporated herein by reference as if set forth in its entirety.

FIELD

The present inventive concept relates generally to blood flow and perfusion quantification and, more particularly, to quantification of blood flow and perfusion in terms of distribution of blood velocity and blood flow rate in tissue/organs using imaging techniques, such as Laser Speckle Imaging, Laser Doppler Imaging and the like with multi-spectral capability.

BACKGROUND

The measurement results of blood flow and perfusion imaging technologies are typically disrupted by a motion artifact of the target tissue/organ in clinical circumstances. This movement can be micro (i.e., pulsatility of an arteriole due to systole and diastole blood pressure levels), intermediate (i.e., normal peristalsis of the small or large bowel) or macro (i.e., the movement of the heart during the cardiac cycle). This movement can be intrinsic to the imaged tissue (i.e., examples cited above), or extrinsic (i.e., the movement of the heart as a result of the movement of the lungs during ventilation). Thus, in many clinical situations, where accurate quantification of flow and perfusion is desirable, keeping the imaging target in a stationary status is difficult and, in some clinical scenarios, is not even possible. For example, such as imaging the distribution of blood flow velocity and flow rate for quantifying perfusion in coronary arteries and myocardium of a beating heart. Unfortunately, most conventional laser-based perfusion technologies either assume the target tissue/organ is stationary, which introduces significant inaccuracy or error in the clinical measurement of blood speed or velocity where the target is moving, such as a beating heart, or simply provide no information for quantification of perfusion in terms of blood flow rate distribution that is critically needed in the clinical situation where the target may or may not be moving.

Tissues/organs in animals or humans respond differently to light of different wavelengths. In general, light of shorter wavelengths can penetrate only the superficial layers of the tissues while light of longer wavelengths can penetrate both superficial layers and sub-surface layers in the spectral region from ultraviolet (UV) to near-infrared (NIR). UV and visible light of wavelengths less than, for example, 550 nm is optimal for detailed anatomic visualization in medicine when viewing the surface of tissues and organs. However, unlike NIR light, UV or visible light imaging is usually not inherently capable of revealing the physiological characteristics of tissues/organs in sub-surface layers, in part due to lack of penetration of the tissues/organs. Accordingly, improved methods of visualization and quantification are desired.

SUMMARY

Some embodiments of the present inventive concept provide a multispectral imaging system. The system includes a first light source having a first wavelength configured to image a sample; a second light source, different from the first light source, having a second wavelength, different from the first wavelength, configured to image the sample; at least a third light source, different from the first and second light sources, having a third wavelength, different from the first and second wavelengths, configured to image the sample; a camera configured to receive information related to the first, second and at least third light sources from the sample, wherein light at the first wavelength is configured to image a surface of the sample into the camera; light at the second wavelength is configured to penetrate the sample to a first depth and provide information related to the sample to the camera; and light at least the third wavelength is configured to penetrate the sample to a second depth different from the first depth of the light at the second wavelength; and a processor configured to combine the information related to the first, second and at least third light sources provided by the camera to image an anatomical structure of the sample, image physiology of blood flow and perfusion of the sample and/or synthesize the anatomical structure and the physiology of blood flow and perfusion of the sample in terms of a blood flow rate distribution. The camera is positioned in a region of interest of the sample using an endoscope.

In further embodiments, the endoscope may be configured to provide the information related to the first, second and at least third light sources to the processor and may be included in an endoscopic imaging system. The endoscopic imaging system may include the camera; a control unit configured to control the camera and process images associated therewith; an image management unit configured to display and manipulate the images associated with the camera; and a system interface configured to translate the information related to the first, second and at least third light source to perform within the endoscopic imaging system such that the images associated therewith are displayed and manipulated.

In still further embodiments, the endoscopic imaging system may include at least one of a system for endoscopic surgery including one or more of laparoscopy, thorascoscopy, and cystoscopy; a system for minimally invasive surgical procedures using the endoscope for illumination, visualizing, and manipulation; and a system for robotic procedures using the endoscope for illumination, visualizing, and manipulation.

In some embodiments, the endoscopic imaging system may be configured to illuminate cavity tissues and organs during a procedure; to visualize cavity tissues and organs for surgical intervention; and for surgical manipulation of cavity tissues and organs for surgical intervention.

In further embodiments, the endoscopic system may be configured to illuminate the region of interest using fibers, fiber compositions, fiber arrangements, lenses, diffusers, collimators, and/or expanders. In still further embodiments, the camera may include a plurality sensors and is configured to have speeds, focus, accuracy and fidelity to obtain images using the endoscopic system. The camera may be coupled to the optic fiber in the endoscope.

In some embodiments, the plurality sensors may be arranged along a continuum from an endoscope tip to a distance remote from the endoscope coupled by image capture cabling.

In further embodiments, the endoscope may be one of a rigid endoscope, semi-rigid endoscope and a flexible endoscope.

In still further embodiments, the endoscope may be one of a rigid endoscope having a flexible, navigable tip and a flexible endoscope having a flexible insertion tube.

In some embodiments, the at least third wavelength may be configured to assess a specific physiologic parameter, such as Hgb concentration. The system may be provided as one or more of a hand-held system, a finger probe unit, a skin patch, and a mobile system.

In further embodiments, the multispectral imaging system may include different blood flow and perfusion measurement technologies in one system. The blood flow and perfusion measurement technologies may include one or more of laser speckle imaging (LSI), laser Doppler imaging (LDI), florescence imaging and reflectance imaging.

Still further embodiments of the present inventive concept provided methods for multispectral imaging in a multispectral imaging system adapted for an endoscopic system. The method includes imaging a sample using a first light source having a first wavelength and being delivered through an endoscopic system; imaging the sample using a second light source, different from the first light source, having a second wavelength, different from the first wavelength, and being delivered through the endoscopic system; receiving information related to the first and second light sources from the sample at a camera, wherein light at the first wavelength is configured to reflect off a surface of the sample into the camera and light at the second wavelength is configured to penetrate the sample and provide information related to the sample to the camera through the endoscopic system; and combining the information related to the first and second light sources received by the camera using at least one processor to image an anatomical structure of the sample, image physiology of blood flow and perfusion of the sample and/or synthesize the anatomical structure and the physiology of blood flow and perfusion of the sample in terms of a blood flow rate distribution In some embodiments, the illumination, analysis and display may be performed using the endoscopic system. The endoscopic system may be configured to communicate with a multi-spectral physiologic visualization (MSPV) operating system.

Some embodiments of the present inventive concept provide an endoscopic imaging system. The system includes an endoscope and a light source unit coupled to the endoscope. The light source unit provides first, second and at least a third light source. The first light source has a first wavelength configured to image a sample. The second light source is different from the first light source and has a second wavelength, different from the first wavelength, configured to image the sample. The at least a third light source, different from the first and second light sources, has a third wavelength, different from the first and second wavelengths, configured to image the sample. The system further includes a camera control unit coupled to the endoscope through a camera head of a camera, the camera head being adapted to receive information related to the first, second and at least third light sources, wherein light at the first wavelength is configured to image a surface of the sample into the camera; light at the second wavelength is configured to penetrate the sample to a first depth and provide information related to the sample to the camera and light at the at least third wavelength is configured to penetrate the sample to a second depth and provide information related to the sample to the camera; and an image processing unit coupled to endoscope configured to combine the information related to the first, second and at least third light sources provided by the camera head to image an anatomical structure of the sample, image physiology of blood flow and perfusion of the sample and/or synthesize the anatomical structure and the physiology of blood flow and perfusion of the sample in terms of a blood flow rate distribution.

BRIEF DESCRIPTION OF THE DRAWINGS

FIGS. 7A and 7B are images illustrating the perfusion measurement using only near infra-red light (7A) and dual wavelength illumination 7B) of a moving hand.

FIGS. 8A and 8B are images illustrating the perfusion measurement using only near infra-red light (8A) and dual wavelength illumination (8B) of a stationary hand with blood supply temporarily occluded by inflating an ipsilateral blood pressure cuff.

FIGS. 14A-14E illustrate an image using a visible wavelength (532 nm) (14A); an image using near infra-red wavelength (785 nm) (14B); a reconstructed image (in gray scale) with the visible and infrared wavelengths (14C); a regular image with room light illumination (14D); and an image showing blood flow and perfusion image (14E).

FIGS. 15A-15B, 16A-16B, 17A-17B, 18A-18B, and 19A-19B illustrate images that compensate for issues during clinical imaging procedures in accordance with some embodiments of the present inventive concept.

FIG. 20 is a diagram of a mobile system in accordance with some embodiments of the present inventive concept.

FIG. 31 is a diagram illustrating field of view (FOV) in accordance with endoscopic embodiments discussed herein.

DETAILED DESCRIPTION

Figure 1A:
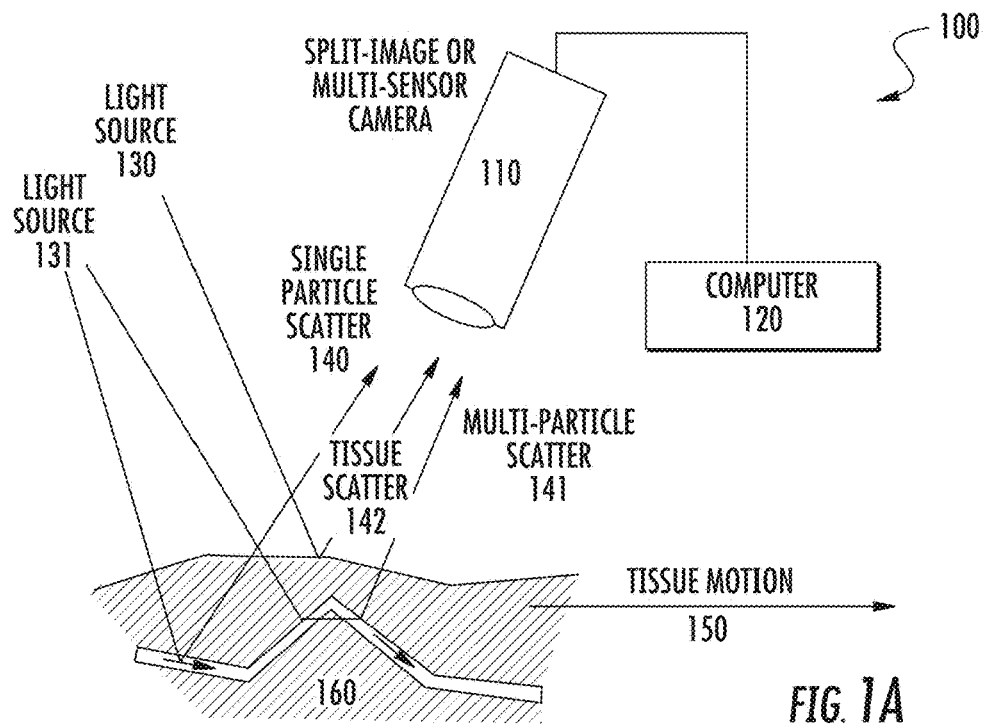
FIG. 1A is a block diagram illustrating a system implementing dual wavelength imaging in accordance with some embodiments of the present inventive concept.

Embodiments of the present inventive concept will now be described more fully hereinafter with reference to the accompanying figures, in which preferred embodiments of the inventive concept are shown. This inventive concept may, however, be embodied in many different forms and should not be construed as limited to the embodiments set forth herein. Like numbers refer to like elements throughout. In the figures, layers, regions, elements or components may be exaggerated for clarity. Broken lines illustrate optional features or operations unless specified otherwise.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y." The term "about" means the numerical value can vary by plus or minus ten percent.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the inventive concept. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

As will be appreciated by one of skill in the art, embodiments of the present inventive concept may be embodied as a method, system, data processing system, or computer program product. Accordingly, the present inventive concept may take the form of an embodiment combining software and hardware aspects, all generally referred to herein as a "circuit" or "module." Furthermore, the present inventive concept may take the form of a computer program product on a non-transitory computer usable storage medium having computer usable program code embodied in the medium. Any suitable computer readable medium may be utilized including hard disks, CD ROMs, optical storage devices, or other electronic storage devices.

Computer program code for carrying out operations of the present inventive concept may be written in an object oriented programming language such as Matlab, Mathematica, Java, Smalltalk, C or C++. However, the computer program code for carrying out operations of the present inventive concept may also be written in conventional procedural programming languages, such as the "C" programming language or in a visually oriented programming environment, such as Visual Basic.

It will be understood that some embodiments of the present inventive concept implemented in Matlab may provide improved processing speeds in accordance with some embodiments of the present inventive concept.

Certain of the program code may execute entirely on one or more of a user's computer, partly on the user's computer, as a standalone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The inventive concept is described in part below with reference to flowchart illustrations and/or block diagrams of methods, devices, systems, computer program products and data and/or system architecture structures according to embodiments of the inventive concept. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

The present inventive concept relates generally to blood flow and perfusion quantification and, more particularly, to quantification of blood flow and perfusion in tissue/organs in terms of distributions of blood velocity and blood flow rate using imaging techniques, such as Laser Speckle Imaging (LSI), Laser Doppler Imaging (LDI), Florescence imaging, reflectance imaging and the like with multispectral capability. Some embodiments of the inventive concept use two or more wavelengths in the range from 350 nm to 1100 nm to measure/quantify the blood velocity and blood flow rate distributions for quantification of perfusion, remove motion artifact and enhance visualization for presentation and real-time evaluation and assessment of the synthesized anatomical-physiological result. As used here, "Multispectral Laser Imaging (MSLI)" refers to imaging techniques using two or more wavelengths in accordance with some embodiments of the present inventive concept.

In particular, some embodiments of the present inventive concept provide a system that uses two wavelengths (or wavelength ranges) of differential transmittance through a sample to apply laser speckle or laser Doppler imaging. A first of the two wavelengths may be relatively small within the UV or visible range, such as blue light 450-495 nm. Light at this wavelength has very shallow penetration and images the anatomical structure of tissue/organ surface and serves as a position marker of the sample but not the subsurface movement of blood flow and perfusion. A second wavelength may be relatively large in the visible (400-700 nm) or near Infra-Red (NIR) range (700-2500 nm). Light at this wavelength has much larger penetration depth and reveals the underlying blood flow physiology and correlates both to the motion of the sample and also the movement of blood flow and perfusion. Using the imaging measurement of the visible light as a baseline, the true motion of blood flow and perfusion can be derived from the NIR imaging measurement without being affected by the motion artifact of the target. Furthermore, the anatomical structure information captured by visible light and the physiological characteristics measured by NIR light is combined as will be discussed herein.

As discussed in the background of the present application, using only visible or NIR spectrums may result in various issues with the final images produced. Accordingly, some embodiments of the present inventive concept combine different wavelengths of visible and NIR spectrum (350 nm 1100 nm) into an imaging system, such as LSI, LDI, Fluorescence, Reflectance or LSI plus Fluorescence and the like. The combination, as discussed herein, may reveal much more information of the tissue/organ than using one single wavelength. In particular, MSLI in accordance with some embodiments discussed herein can (1) account for and remove the motion artifact present in imaging clinical biologic structures, which creates blood flow and perfusion quantification inaccuracies; (2) improve visualization over current technologies by exact synthesis of both anatomic structure and the physiology of blood flow and perfusion simultaneously in real time; (3) through a combination of (1)

and (2), improve the accuracy of quantification of blood flow and perfusion in clinical applications as will be discussed herein with respect to FIGS. 1A through 29B.

As used herein, "real time" refers to provision of data within a very short amount of time, for example, milliseconds, so as to appear as if the data was provided immediately upon request or activation of light sources.

In some embodiments, in addition to using multiple wavelengths over the visible and NIR spectrum (350-1100 nm), embodiments of the present inventive concept can, for example, combine two or more laser imaging techniques such as near infra-red fluorescence (NIRF) and Laser Speckle Imaging (LSI), or NIRF and Laser Doppler Imaging (LDI), into one system as will also be discussed below with respect to the Figures.

Furthermore, some embodiments of the present inventive concept provide the ability to apply methods of visualization and quantification across multiple clinical and experimental settings. These settings include direct illumination and imaging of tissues, but where access to the imaged Field of View (FOV) is accomplished through different approaches. These approaches may include, for example, direct contact or non-contact with tissues, exposure of the tissues during open surgical procedures, or via endoscopy to access tissues within closed anatomic structures or tissues in the alimentary tract or tracheobronchial tree without departing from the scope of the present inventive concept.

Referring first to FIG. 1A, a block diagram illustrating a simplistic system implementing dual wavelength imaging in accordance with some embodiments of the present inventive concept will be discussed. As illustrated in FIG. 1A, the system 100 includes at least two light sources, first 130 and second 131 light sources, respectively, a sample 160, a camera 110 and a communications device (computer 120). In some embodiments of the present inventive concept, the first light source 130 delivers visible light and the second light source 131 delivers NIR light. As discussed above, the coherent short wavelength (visible source 130) does not penetrate deep into the sample 160 (tissue/organ), but provides detail of the surface of the sample 160 in the tissue scatter (142). In contrast, the coherent NIR source 131 penetrates deep into the sample 160 and may provide single (140) or multi particle (141) scatter. The reflections 140, 141, 142 off the sample 160 are captured by a camera 110, which may be, for example, a split-image or multi-sensor camera. In particular, in some embodiments the camera may be a multi-sensor camera, rather than a single camera with one sensor chip. The multi-sensor camera has multiple sensors and each sensor may be configured to image one wavelength or wavelength range. As illustrated in FIG. 1C, in embodiments having a multi-sensor camera 110', the camera may have a plurality of spaced apart sensors S1 through SN. Each sensor may be configured to image one wavelength or wavelength range. The number "N" in S1-SN can be any reasonable number in accordance with embodiments discussed here. For example, "N" may be between 2 and 50.

The information can be processed by the communications device 120, which combines the visible and NIR wavelength images to provide improved blood flow and profusion data in accordance with some embodiments of the present inventive concept. As will be understood, the data provided by embodiments discussed herein account for movement 150 of the sample (tissue/organ) 160 and provide a much improved image thereof.

Although some embodiments are discussed herein as having two wavelengths, embodiments of the present inventive concept are not limited to this configuration. For example, as illustrated in the system 100' in FIG. 1B, in some embodiments, at least a third light source 132 is provided having a third wavelength and this wavelength may penetrate the sample a different depth than the first and second wavelengths and provide a different scatter pattern 143. In some embodiments, the at least third wavelength may be configured to assess a specific physiologic parameter, for example, Hgb concentration. It will be understood that there may more than three light sources in some embodiments.

Figure 2:
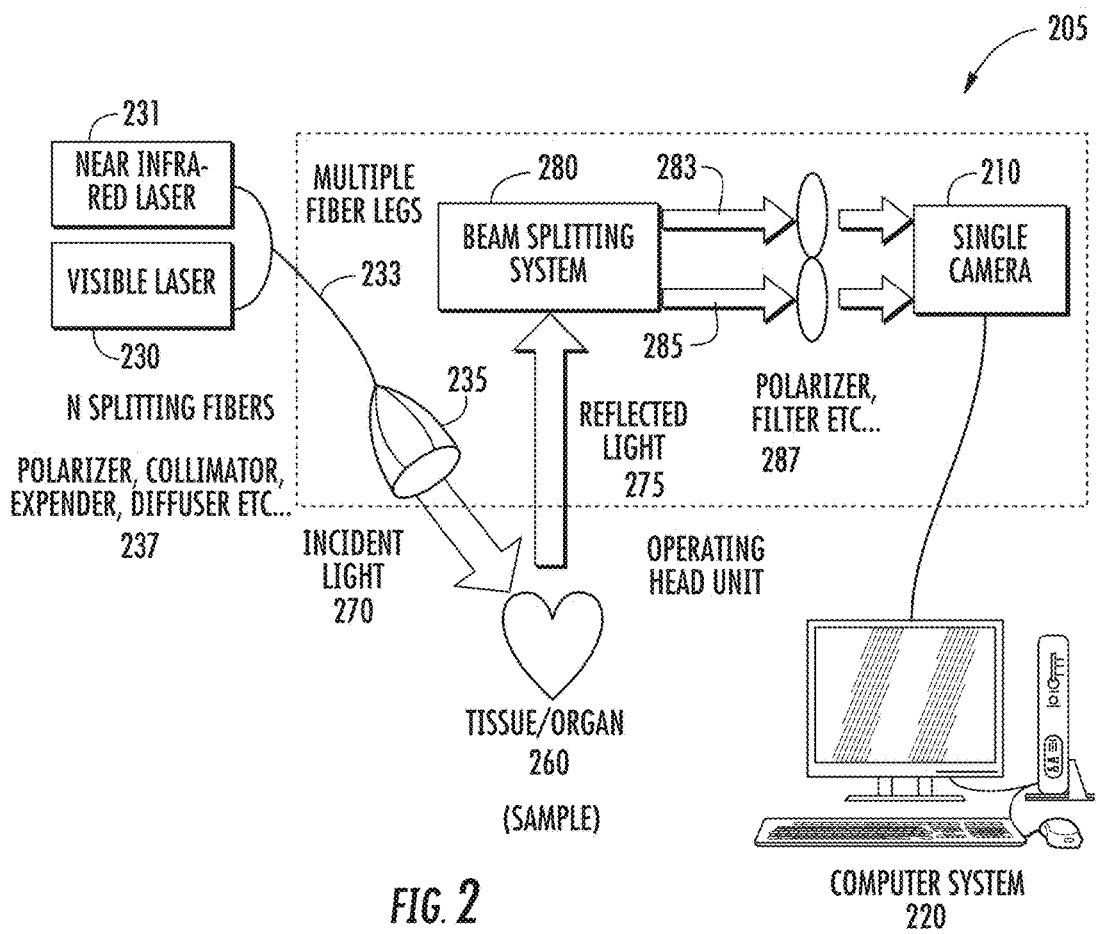
FIG. 2 is a more detailed block diagram illustrating various components of a multi-wavelength imaging system in accordance with some embodiments of the present inventive concept.

Referring now to FIG. 2, a more detailed block diagram illustrating various components of a multi-wavelength imaging system in accordance with some embodiments of the present inventive concept will be discussed. As illustrated in FIG. 2, the system 205 includes at least two laser light sources, visible 230 and NIR 231, a connecting fiber 233, components of an imaging system 237, a sample 260, a beam splitter 280, a camera 210 and a communications device (computer system 220). In operation, when the NIR laser delivers NIR light to a living sample 260, such as a tissue/organ, a portion of the NIR light will go through single or multiple scattering of both stationary and moving particles inside the sample and reflect back. When the visible laser 230 delivers non-penetrating visible light, such as light having 430 nm, to a living sample 260, such as a tissue/organ, most of the light will be reflected back by the surface within less than 100 μm depth. For the NIR laser 231, approximately ninety five percent of the light will be returned from a top 700 μm of the sample 260, which is enough penetration to pass through coronary artery walls at, for example, a 300 μm depth, and generate information from moving particles, such as red blood cells, as well as from stationary tissue.

The reflected visible light contains the surface movement information of the sample 260 and, thus, reflects the motion artifact. The reflected NIR light contains the surface and subsurface movement information of the sample 260 and, thus, reflects both motion artifact and movement of the blood flow. As illustrated in FIG. 2, the light produced by the lasers 230 and 231 may be provided to a fiber 233, which may have multiple fiber legs and may include a plurality of splitting fibers 235 as illustrated. However, embodiments of the present inventive concept are not limited to the configuration illustrated in FIG. 2. For example, more or less fibers may be used without departing from a scope of the present inventive concept. Furthermore, the light on the fibers may pass through various elements of an imaging system 237 before reaching the sample 260. For example, the light may traverse polarizers, collimators, expanders, diffusers and the like before reaching the sample 260 without departing from the scope of the present inventive concept.

The incident light 270 illuminates the sample 260 and the reflected light 275 is provided to a beamsplitter 280. In some embodiments of the present inventive concept, the beamsplitter 280 may be a dichroic beam splitting system that separates the NIR 283 and visible light 285. The separated light 283 and 285 may pass through polarizers, filters and the like 287 before being delivered to the camera 210. As discussed above, the camera 210 can be, for example, a split-image (single sensor) or multi-sensor camera without departing from the scope of the present inventive concept. As stated, the multi-sensor camera has multiple sensors each configured to image a wavelength or wavelength range.

The NIR 283 and visible 285 images are directed to the camera 210 and a split image is created on one camera sensor or on separate camera sensors S1-SN (FIG. 1C) that have been synchronized and aligned. As discussed above, different wavelengths have different penetration levels in the tissue/organ. Using multi-spectrum image design as discussed herein, the anatomical structure and blood flow physiology at different depths in the tissue/organ can be revealed as will be discussed below with respect to various figures.

Figure 1B:
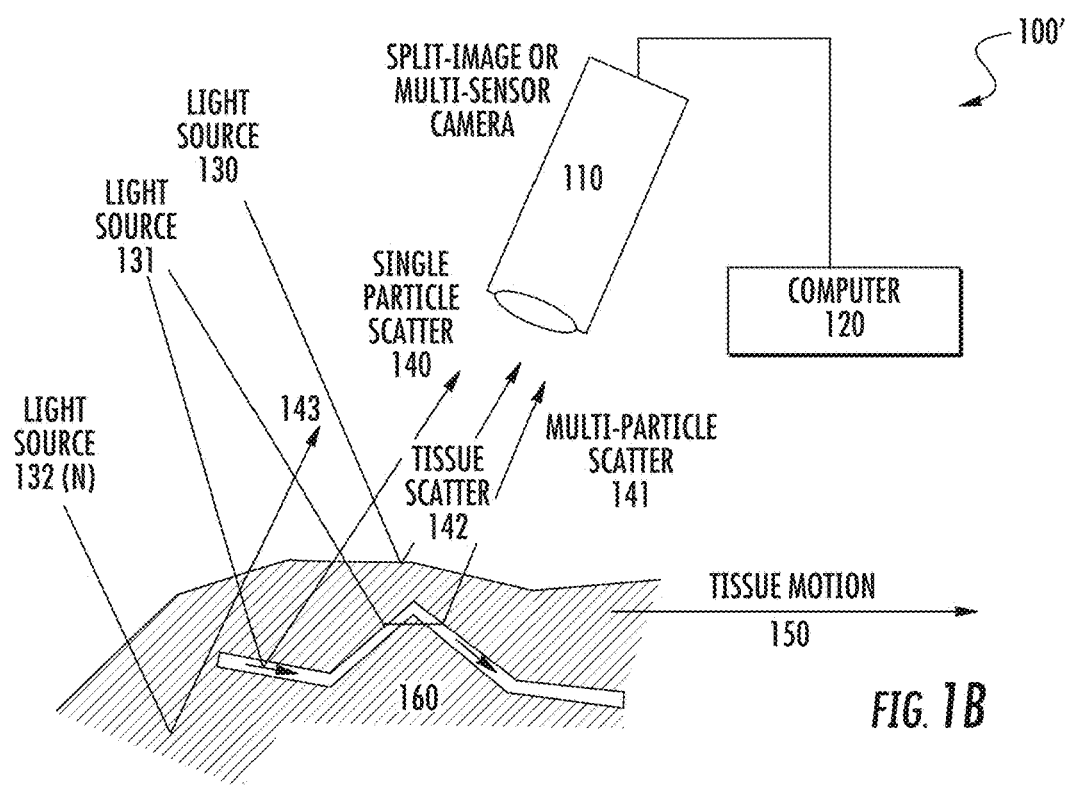
FIG. 1B is a block diagram illustrating a system including multiple light sources in accordance with some embodiments of the present inventive concept.
Figure 1C:
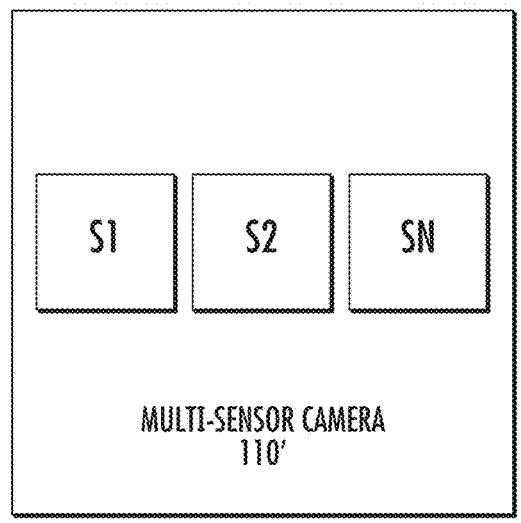
FIG. 1C is a block diagram illustrating a multi-sensor camera in accordance with some embodiments of the present inventive concept.
Figure 3:
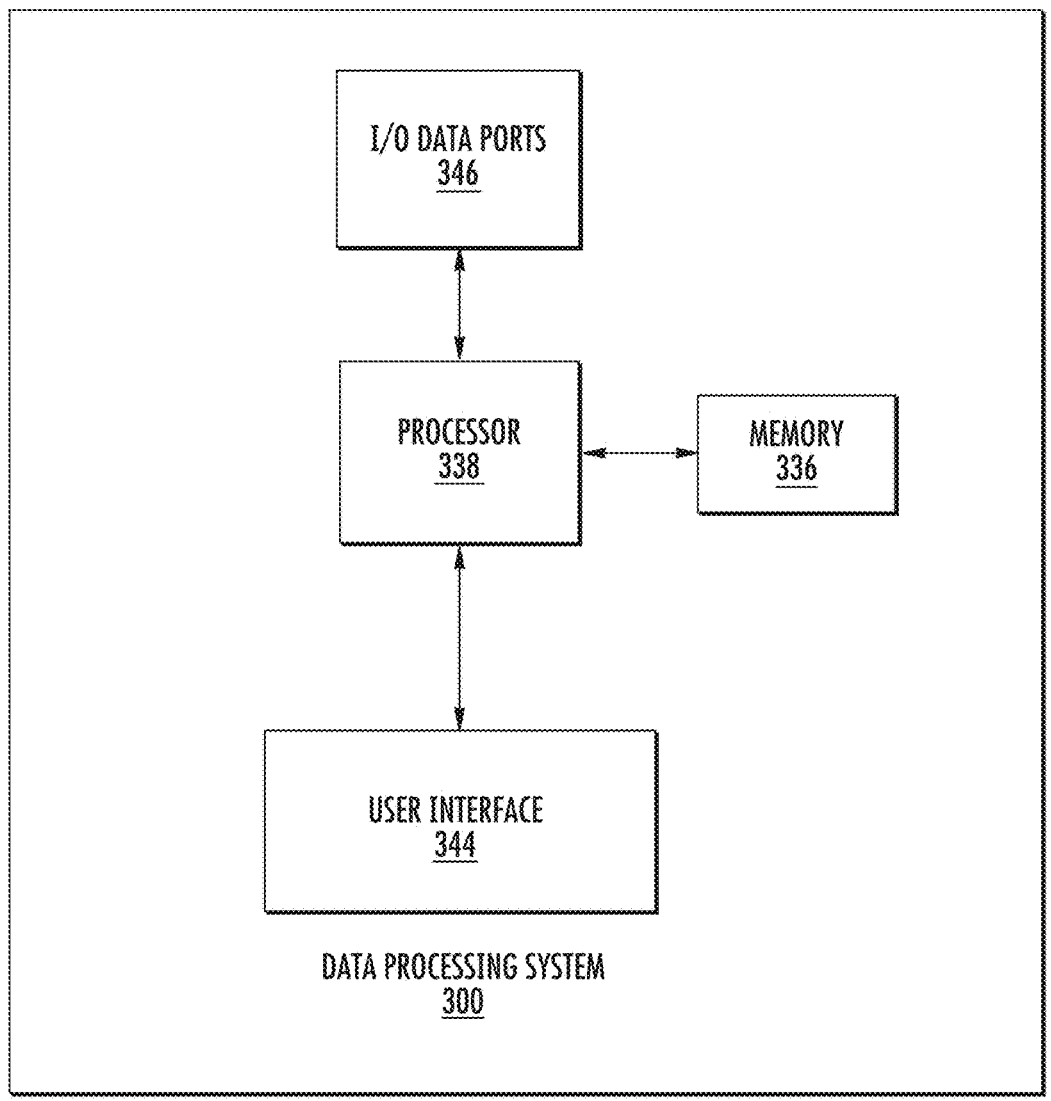
FIG. 3 is a block diagram of a data processing system according to some embodiments of the present inventive concept(s).

As illustrated in FIGS. 1A, 1B and 2, systems in accordance with embodiments of the present inventive concept include communications devices 120, 220, which are used for the various processing necessary to implement embodiments of the present inventive concept. Referring now to FIG. 3, a data processing system 300 that may be used in the systems of FIGS. 1 and 2, for example, in the communications devices 120, 210, in accordance with some embodiments of the inventive concept will be discussed. It will be understood that the data processing system 300 may be included in any of the components of the system without departing from the scope of the present inventive concept. For example, the data processing system 300 may be included in the camera 110, 210 or split between various elements of the system without departing from the scope of the present inventive concept.

Referring now to FIG. 3, an exemplary embodiment of a data processing system 300 suitable for use in the systems of FIGS. 1 and 2 includes a user interface 344 such as a keyboard, keypad, touchpad or the like, I/O data ports 346 and a memory 336 that communicates with a processor 338. The I/O data ports 346 can be used to transfer information between the data processing system 300 and another computer system or a network. These components may be conventional components, such as those used in many conventional data processing systems, which may be configured to operate as described herein.

Figure 4:
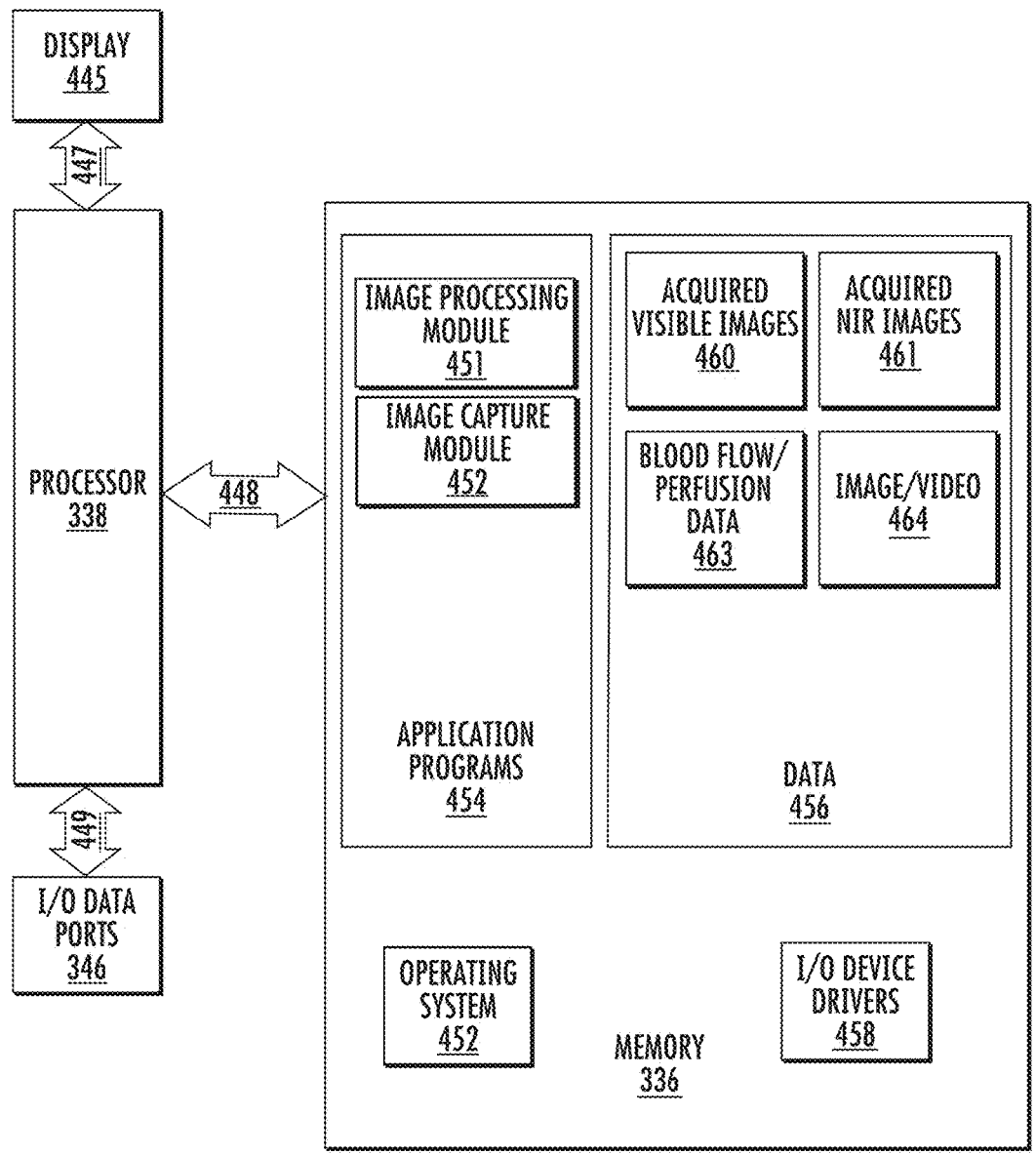
FIG. 4 is a more detailed block diagram of the data processing system illustrated in FIG. 3 in accordance with some embodiments of the present inventive concept(s).

Referring now to FIG. 4, a more detailed block diagram of the data processing system 400 in accordance with some embodiments of the present inventive concept will be discussed. The processor 338 communicates with a display 445 via and address/data bus 447, the memory 336 via an address/data bus 448 and the I/O data ports 346 via an address/date bus 449. The processor 338 can be any commercially available or custom microprocessor or ASICs. The memory 336 is representative of the overall hierarchy of memory devices containing the software and data used to implement the functionality of the data processing system 400. The memory 336 can include, but is not limited to, the following types of devices: cache, ROM, PROM, EPROM, EEPROM, flash memory, SRAM, and DRAM.

As illustrated in FIG. 4, the memory 336 may include several categories of software and data used in the data processing system 400: an operating system 452; application programs 454; input/output (I/O) device drivers 458; and data 456. As will be appreciated by those of skill in the art, the operating system 452 may be any operating system suitable for use with a data processing system, such as OS/2, AIX or zOS from International Business Machines Corporation, Armonk, N.Y., Windows95, Windows98, Windows2000, WindowsXP, or Vista from Microsoft Corporation, Redmond, Wash., Unix, Linux, LabView, or a real-time operating system such as QNX or VxWorks, or the like. The I/O device drivers 458 typically include software routines accessed through the operating system 452 by the application programs 454 to communicate with devices such as the I/O data port(s) 346 and certain memory 336 components. The application programs 454 are illustrative of the programs that implement the various features of the data processing system 400 included in a system in accordance with some embodiments of the present inventive concept and preferably include at least one application that supports operations according to some embodiments of the present inventive concept. Finally, the data 456 represents the static and dynamic data used by the application programs 454, the operating system 452, the I/O device drivers 458, and other software programs that may reside in the memory 336.

As illustrated in FIG. 4, the data 456 according to some embodiments of the present inventive concept may include acquired visible images 460, acquired NIR images/data 461, calculated blood flow/perfusion data 463 and images/video 464. Although the data 456 illustrated in FIG. 4 includes four different files 460, 461, 463 and 464, embodiments of the present inventive concept are not limited to this configuration. Two or more files may be combined to make a single file; a single file may be split into two or more files and the like without departing from the scope of the present inventive concept.

As further illustrated in FIG. 4, the application programs 454 may include an image processing module 451 and an image capture module 452 in accordance with some embodiments of the inventive concept. While the present inventive concept is illustrated, for example, with reference to the image processing module 451 and the image capture module 452 being application programs in FIG. 4, as will be appreciated by those of skill in the art, other configurations may also be utilized while still benefiting from the teachings of the present inventive concept. For example, the image processing module 451 and the image capture module 452 may also be incorporated into the operating system 452 or other such logical division of the data processing system 400. Thus, the present inventive concept should not be construed as limited to the configuration of FIG. 4, but is intended to encompass any configuration capable of carrying out the operations described herein.

Furthermore, while the image processing module 451 and the image capture module 452 are illustrated in a single data processing system, as will be appreciated by those of skill in the art, such functionality may be distributed across one or more data processing systems. Thus, the present inventive concept should not be construed as limited to the configurations illustrated in FIGS. 3 and 4, but may be provided by other arrangements and/or divisions of function between data processing systems.

In certain embodiments, such as an LSI application, the velocity of a target fluid can be calculated using the following equation:

$$v(i, j) = v_0 + \frac{a}{c(i, j)^2} \qquad \text{Eqn. (1)}$$

where $v(i, j)$ is the velocity of target fluid, $v_0$ is an added term to account for background noise and may be zero after the baseline has been removed; $\alpha$ is a constant related to imaging parameters, laser parameters, time/spatial smoothing parameters for obtaining c and reflects the optical characteristics of the target fluid; c is the laser speckle contrast; and i and j are the row and column pixel index.

For an LDI application, the velocity of a target fluid can be calculated using the following equation:

$$v(i, j) = \frac{\lambda}{2\sin\theta} \Delta f \qquad \text{Eqn. (2)}$$

where v(i, j) is velocity of target fluid; where $\lambda$ is the wavelength; $\Delta f$ is the change in Doppler frequency (Doppler frequency shift); and $\theta$ is half of the angle between the two beams. Typically, there is no direct formula to apply for NIRF, and the like.

However, even when the imaged object is stationary, there is movement present that must be accounted for to accurately determine blood flow in vessels and perfusion in tissue. As recently as 2013, experts in the field of LSI discussed motion artifact as one of the two key questions still to be answered in this field. Therefore, systems and methods that have the capability to identify this motion contribution and account for its magnitude are needed and included in technologies claiming to be able to assess, image, and/or quantify blood flow in vessels and perfusion in tissues experimentally and in vivo.

Figure 5A:
FIGS. 5A and 5B are a visible light image (5A) and a near infra-red light image (5B) of a hand.
Figure 5B:
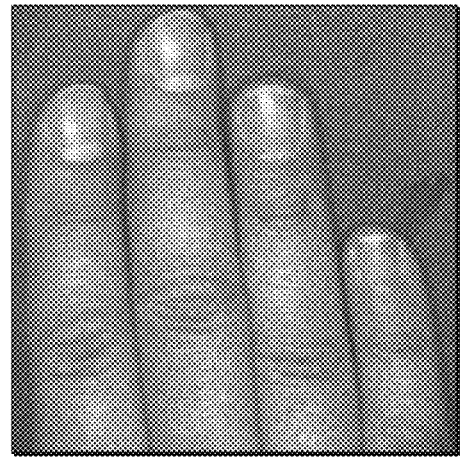

Referring now to FIGS. 5A and 5B, FIG. 5A is a visible light image of a hand and FIG. 5B is a near infra-red light image of a hand. These images may be used to calculate the motion artifact and the movement of the blood flow and perfusion in accordance with some embodiments of the present inventive concept.

In particular, to remove the motion artifact of the tissue/organ that is caused by movement of tissue/organ, such as aspiration, spasm, heart beat and the like and/or the camera, Galilean velocity addition can be calculated using the following equation:

$$v_{12}(r) = v_{13}(r) + v_{32}(r) = v_{13}(r) - v_{23}(r) \qquad \text{Eqn. 3}$$

where: $v_{13}(r)$ is the velocity distribution of object of interest (blood flow and perfusion) relative to detector (camera); $v_{23}(r)$ is the velocity distribution of the host object (the tissue/organ in which the blood vessel is embedded) relative to detector (camera); $v_{32}(r)$ is the velocity distribution of the detector (camera) relative to the host object (the tissue/organ in which the blood is embedded); and $v_{12}(r)$ is the velocity distribution of an object of interest (blood flow and perfusion) relative to the host object (the tissue/organ in which the blood vessel is embedded). In other words, $v_{32}(r)$ and $v_{23}(r)$ Thus, embodiments of the present inventive concept may address a need to determine $v_{12}(r)$ under the condition that the image signals by the all the current LSI or LDI method provides only $v_{13}(r)$. According to some embodiments of the present inventive concept, the multi spectrum imaging approach, both $v_{13}(r)$ and $v_{23}(r)$ can be made available.

Using LSI as an example, using the Eqn. (1) above, the speckle contrast of coherent NIR laser light $C_{NIR}(i, j)$ is associated with $v_{13}(r)$, which is the velocity distribution of an object of interest (blood flow and perfusion) relative to detector (camera). $v_{13}(r)$ is affected by the movement of blood flow and the movement of tissue/organ caused by factors such as aspiration, spasm, heart beat etc. and the movement of the camera. The visible laser light, especially within the 450~495 nm wavelength range (blue laser light), has much less penetration in soft tissue/organ compared with the NIR laser light.

Using Eqn. (1) set out above, the speckle contrast of coherent visible laser light $C_{VIS}(i, j)$ is mainly associated with $v_{23}(r)$, which is the velocity distribution of the host object (the tissue/organ that the blood vessel is embed) relative to detector (camera). $v_{23}(r)$ is affected by the movement of tissue/organ caused by factors such as aspiration, spasm, heart beat etc. and the movement of the camera. Using Eqn. (3), $v_{12}(r)$ can be derived using $v_{13}(r)$ and $v_{23}(r)$ thus the velocity distribution of object of interest (blood flow and perfusion) relative to the host object (the tissue/organ that the blood vessel is embed) can be quantified without the effect of the movement of tissue/organ and the movement of the camera.

The speckle contrast of coherent visible laser light $C_{VIS}(i, j)$ as a baseline can be used to normalize the speckle contrast of coherent NIR laser light $C_{NIR}(i, j)$ based on this mathematic model to reduce the velocity component of the motion artifact. Computer algorithms may be designed to normalize (subtract or divide) $C_{NIR}(i, j)$ using $C_{VIS}(i, j)$ to yield one or multiple stabilized blood flow and perfusion maps in real time. The algorithms may be processed by, for example, a data processor as discussed above with respect to FIGS. 3-4.

Figure 6A:
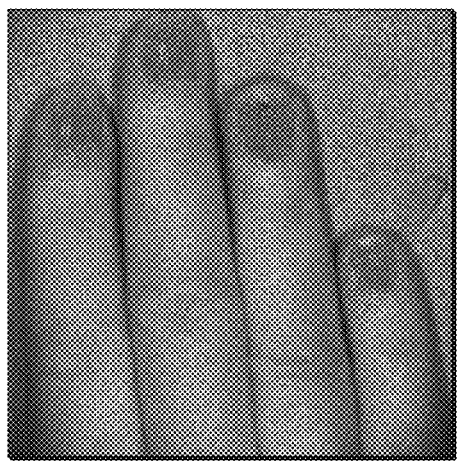
FIGS. 6A and 6B are images illustrating the perfusion measurement using only near infra-red light (6A) and dual wavelength illumination (6B) of a stationary hand.
Figure 6B:
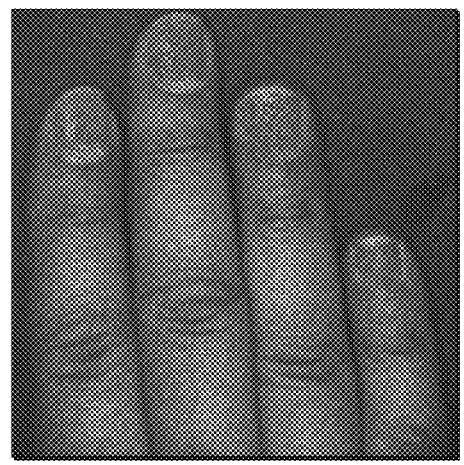

Referring now to FIGS. 6A and 6B, images generated using the measurement of the blood flow and perfusion using only NIR and dual wavelength illumination of a stationary hand will be discussed. As illustrated, the measurement of the blood flow and perfusion using only NIR and dual wavelength illumination of a stationary hand are very similar. This is because when the sample/target is stationary, the motion artifact as baseline measured by visible light is close to zero. Thus, the result without removing the baseline (FIG. 6A: using only NIR light) and the result with the baseline removed (FIG. 6B: using dual wavelength illumination) are almost identical.

Referring now to FIGS. 7A and 7B, images illustrating the measurement of the blood flow and perfusion using only NIR and dual wavelength illumination of a moving hand will be discussed. As illustrated therein, the measurement of the blood flow and perfusion using only NIR and dual wavelength illumination of a shaking hand are very different. The measurement with only NIR light (FIG. 7A) shows much higher perfusion level which is caused by the motion artifact. The measurement with dual wavelength illumination (FIG. 7B) is almost identical to the measurement of the stationary hand. This is because when the sample/target is moving the motion artifact as baseline measured by visible light is not zero. Thus, the result without removing the baseline (FIG. 7A: using only NIR light) shows more "blood flow and perfusion" than the result with the baseline removed (FIG. 7B: using dual wavelength illumination).

Referring now to FIGS. 8A and 8B, images illustrating both the perfusion measurement with only NIR and the dual wavelength illumination will be discussed. In particular, FIGS. 8A and 8B are images illustrating the perfusion measurement using only near infra-red light (8A) and dual wavelength illumination (8B) of a stationary hand with blood supply temporarily occluded by squeezing the wrist of the imaged hand using the other hand. As illustrated, a decrease induced by the temporary occlusion of the blood supply to the hand is clear.

Different from LSI, LDI uses interference of two coherent light beams: the one from the laser as the light source and the one reflected from the moving object whose frequency is slightly shifted from that of the incident light. LDI determines the speed of one "pixel" or points or a small region of the object where the incident beam is focused on. An image is obtained by scanning the focused beam. Similar to the LSI of Eqn. (1) using Eqn. (2), measurement of $v_{13}(r)$ and $v_{23}(r)$ in LDI can be achieved using a penetrating NIR beam and a non-penetrating visible beam. Again, using Eqn. (3) $v_{12}(r)$ of the fiducial points relative to the host object (the tissue/organ that the blood vessel is embed) can be identified.

Figure 9A:
FIGS. 9A and 9B illustrated perfusion measurement using only near infra-red light (9A) and dual wavelength illumination (9B) of a large bowel of a pig.
Figure 9B:
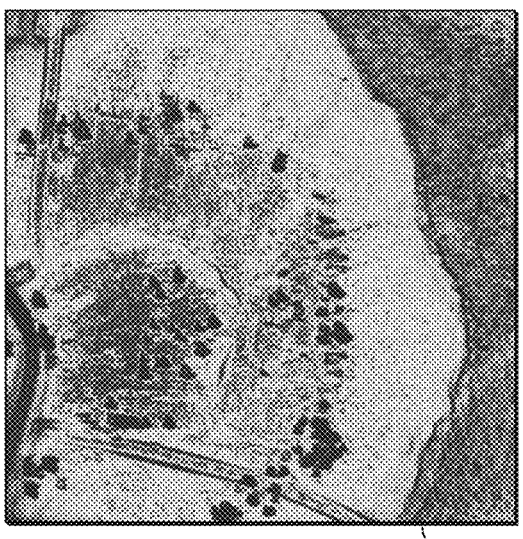

Furthermore, practically, the laser speckle contrast is a mixture of static background and dynamic part. The dynamic part of the speckle contrast is associated with the motion and the static background is caused by the difference of the optical characteristics of the inhomogeneous scattering media. Since among the current LSI technologies, baseline speckle contrast at a no flow situation is not available, other than in a controlled phantom/tubing experiment, the static background of the speckle contrast is a major obstacle to accurately quantifying blood flow in tissue/organ. Multi-spectrum illumination schemes provide a baseline speckle contrast at no flow situation $C_{VIS}(i, j)$ using visible coherent laser light. The speckle contrast of coherent visible laser light $C_{VIS}(i, j)$ can be used to normalize the speckle contrast of coherent NIR laser light $C_{NIR}(i, j)$ based a mathematic model in accordance with embodiments of the present inventive concept to reduce the static background in the speckle contrast as illustrated in FIGS. 9A and 9B. FIGS. 9A and 9B illustrate perfusion measurement using only near infra-red light (9A) and dual wavelength illumination (9B) of a large bowel of a pig. Measurement inaccuracy caused by the static contrast can be seen on the surgical drape 950 in FIG. 9A. In FIG. 9B, the "fake" blood flow and perfusion is not visible on the surgical drape 950 due to reduction of the static contrast.

Embodiments of the present inventive concept propose the visualization of both anatomical structure and blood flow physiology of the tissue and organ by one of two approaches. However, it will be understood that embodiments of the present inventive concept are not limited to the approaches discussed herein.

Figure 10A:
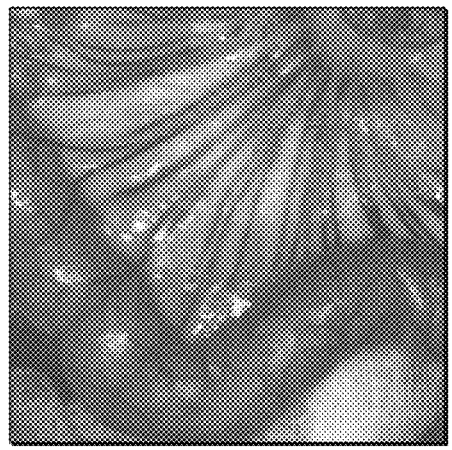
FIGS. 10A-10D are images illustrating a visible light image of a piece of small bowel of a pig as to define anatomical structure (10A); a near infra-red light image of the same piece of small bowel as to define the transparency map (10B); blood flow speed distribution map of the same piece of small bowel calculated by 11 frames of the NIR raw images using LSI (10C); and a combined visual effect using A, B, C using an algorithm in accordance with some embodiments of the present inventive concept to reveal both anatomical structure and blood flow physiology (10D).

Referring now to FIG. 10A-10D, a first approach using a dual layer design will be discussed. Referring first to FIG. 10A (Panel A), an anatomical layer represented by a raw (original) image frame of visible light is illustrated. (Anatomical layer) $Img_{VIS}(i, j)$ is an 8 bit gray scale visible image of the sample/target tissue/organ and i and j are the pixel indexes along the horizontal and vertical direction. In some embodiments, the brightness, contrast and gamma value of this image might be adjusted to achieve better visualization effect.

Figure 10B:
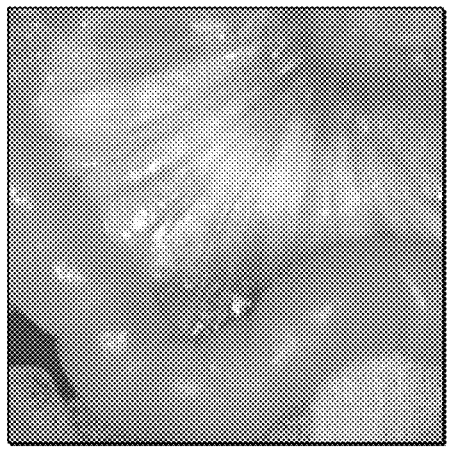

Referring now to FIG. 10B, a processed image is produced based on one or more raw image frames of near infra-red light to reflect two-dimensional (2D) speed distribution of blood flow and perfusion of the imaged tissue/organ using Laser Speckle or Laser Doppler Imaging technology. (Physiological layer) $Img_{NIR}(i, j)$ is an 8bit indexed image with its numerical values mapped to a predefined color map. Usually, the color ranges from blue to red (0 to 255) with blue representing no/minimum flow speed and red representing the highest flow speed that the system can detect.

Figure 10C:
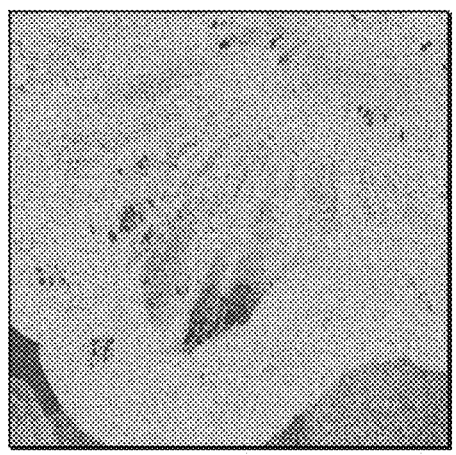
Figure 10D:
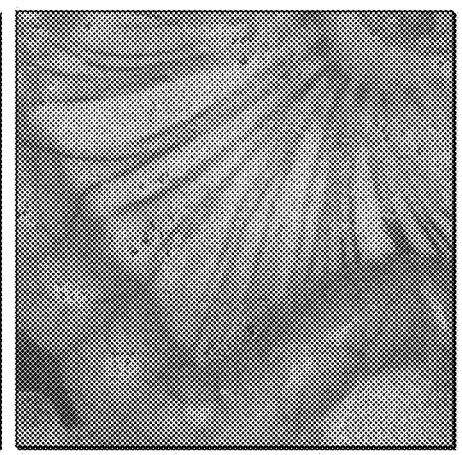

Referring now to FIG. 10C, a transparency map is produced using methods that overlap the anatomical layer or parts of the anatomical layer over a physiological one, which will cause the bottom layer to be invisible (covered) or partially invisible (covered). Methods that overlap the physiological layer or parts of the physiological layer over anatomical one will cause the bottom layer to be invisible (covered) or partially invisible (covered). A transparency map/matrix is applied in accordance with embodiments of the present inventive concept to ensure the visibility of both layers using the following equation:

$$T(i, j) = \left( \frac{Img(i, j) - \text{Min}(Img(i, j))}{\text{Max}(Img(i, j)) - \text{Min}(Img(i, j))} \right)^x \quad \text{Eqn. (4)}$$

where T (i, j) is the transparency map with Img being a raw (original) image frame of visible or near infra-red light and x being an adjustable parameter >0 and <=2. Basically, each pixel value in T(i, j) is between 0 and 1 with 0 representing no transparency and 1 representing 100% transparency. Parameter x controls the contrast of the transparency map and if x>1, transparency has a larger dynamic range and if x<1, the transparency has a smaller dynamic range. FIG. 10D represents the combined visual effect using A, B and C in accordance with embodiments of the present inventive concept to reveal both anatomical structure and physiology.

Figure 11A:
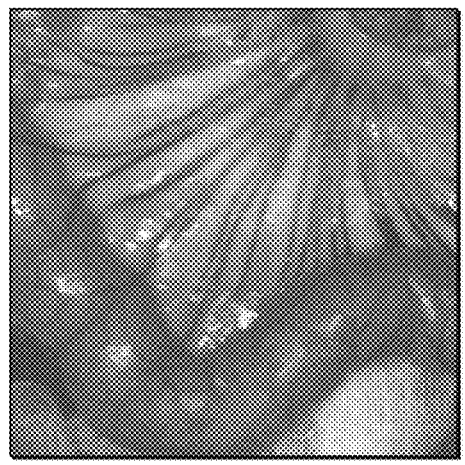
FIGS. 11A-11C are images illustrating a visible light image of a piece of small bowel of a pig as to define anatomical structure by the brightness of the 8 bit grayscale image (11A); blood flow speed distribution map of the same piece of small bowel calculated by 11 frames of the NIR raw images using LSI (11B); and a combined visual effect using A and B using an algorithm in accordance with some embodiments of the present inventive concept to reveal both anatomical structure and blood flow physiology (11C).
Figure 11B:
Figure 11C:
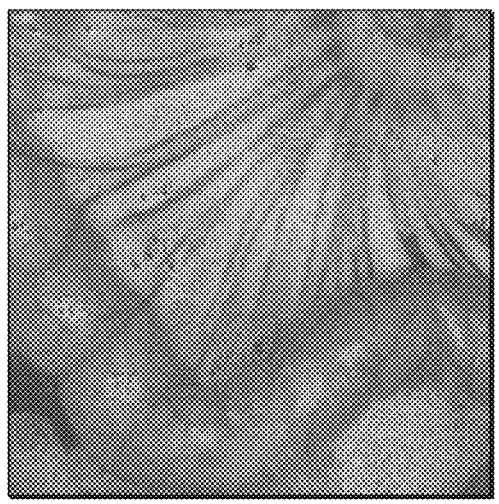

Referring now to FIGS. 11A through 11C, a second approach using color and brightness design will be discussed. As illustrated in FIG. 11A, an anatomical layer is represented by image brightness: a raw (original) image frame of visible light. $Img_{VIS}(i, j)$ is an 8 bit gray scale visible image of the sample/target tissue/organ and i and j are the pixel indexes along horizontal and vertical direction. The brightness, contrast and gamma value of this image may be adjusted to achieve better visualization effect.

Referring now to FIG. 11B, a physiological layer is represented by image color: a processed image based on one or more raw image frames of near infra-red light to reflect 2D speed distribution of blood flow velocity and perfusion of the imaged tissue/organ using Laser Speckle or Laser Doppler Imaging technology. In a first step, an 8 bit indexed color image is generated with its numerical values mapped to a predefined color map. Usually, the color ranges from blue to red (0 to 255) with blue representing no/minimum flow speed and red representing the highest flow speed that the system can detect. In a second step, the 8 bit indexed color image is converted to a normalized RGB map $RGB_{NIR}(i, j)$ with the color of each pixel being represented by (R, G, B) three values and each value range from 0~1. It will be understood that since the Figures are in black and white, the corresponding grey scale has been employed herein.

Referring now to FIG. 11C, anatomical and physiological layers are fused together by creating an 8 bit RGB color image as $Img(i, j) = Img_{VIS}(i, j) \times RGB_{NIR}(i, j)$. Note, each color channel (matrix $R_{NIR}(i, j)$, $G_{NIR}(i, j)$ and $B_{NIR}(i, j)$) is multiplied by the same visible image $Img_{vis}(i, j)$.

According to some embodiments of the present inventive concept, multi wavelength imaging design may be used to simultaneously combine different imaging technologies together. For example, as discussed herein, NIR fluorescence technology based on indocyanine green uses 808 nm illumination and the fluorescence emission light is 830 nm and 808 nm reflection light is considered as noise and filtered out. In accordance with some embodiments of the present inventive concept, the 808 nm reflection light can be used to achieve LSI or LDI while maintaining the 830 nm fluorescence function.

Referring now to FIGS. 12A-12D, images illustrating Panel A, an NIR 785 nm image of a small bowel (12A); Panel B a Green 532 nm image of the same small bowel (12B); Panel C, a reconstructed color image of the same small bowel (12C); and Panel D, an image of the same small bowel taken by a regular camera (12D) will be discussed. In particular, using the multi spectral imaging system in accordance with some embodiments of the present inventive concept, an original color image can be constructed by using each spectrum as one RGB color channel. For example, using an NIR image as a red color channel and a 532 nm image as a green color channel, the color image of a small intestine can be generated without using a color camera as illustrated in FIGS. 12A-12D. It will be understood that since the Figures are black and white, the corresponding grey scale has been employed herein.

Figure 12A:
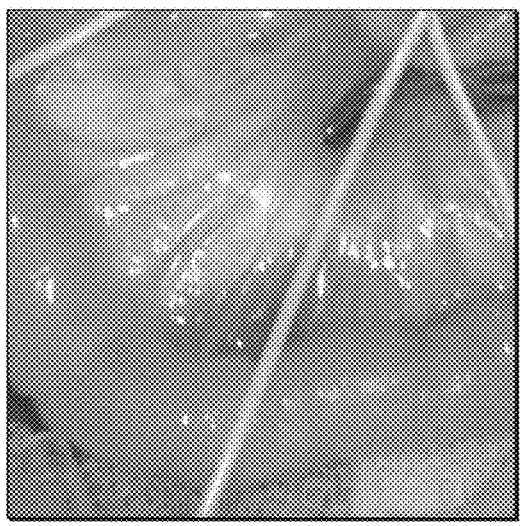
FIGS. 12A-12D are images illustrating Panel A, an NIR 785 nm image of a small bowel (12A); Panel B a Green 532 nm image of the same small bowel (12B); Panel C, a reconstructed image of the same small bowel (12C); and Panel D, an image of the same small bowel taken by a regular camera (12D).
Figure 12B:
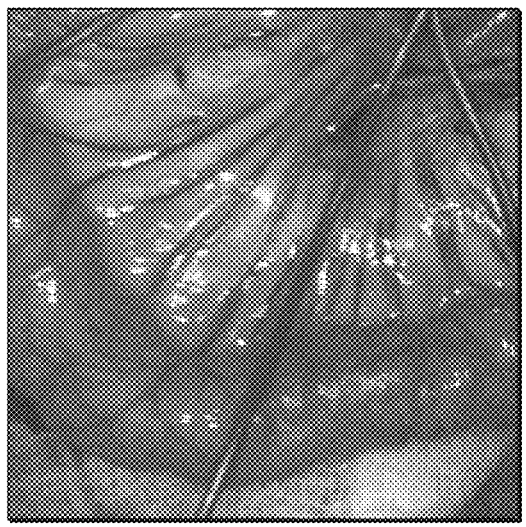
Figure 12C:
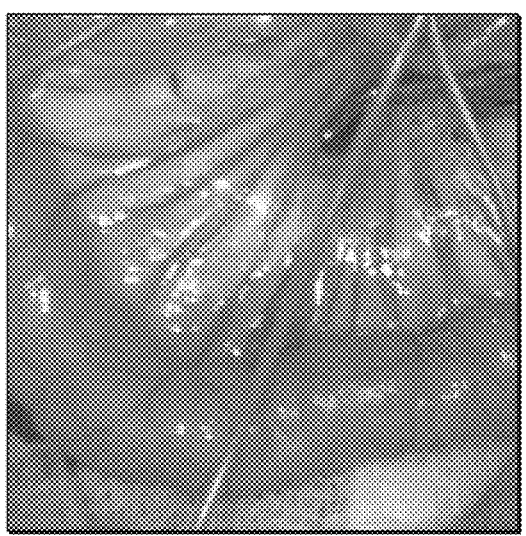
Figure 12D:
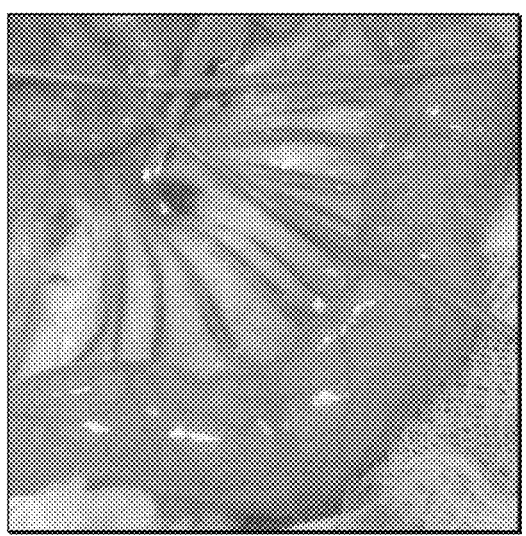
Figure 13A:
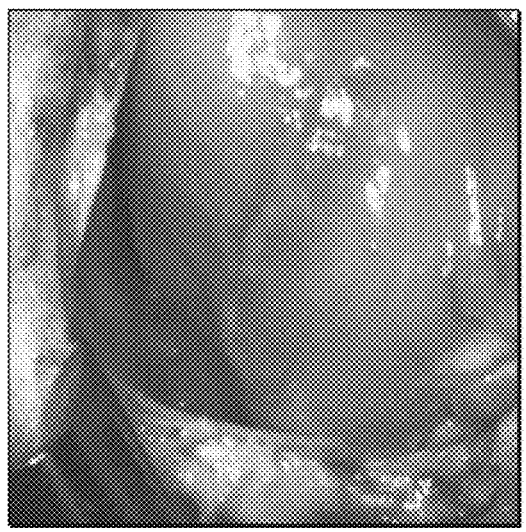
FIGS. 13A-13D are images illustrating Panel A, an NIR 785 nm image of a pig heart (13A); Panel B, Green 532 nm image of the same pig heart (13B); Panel C, a reconstructed image of the same pig heart (13C); and Panel D, an image of the same pig heart taken by a regular camera (13D).
Figure 13B:
Figure 13C:
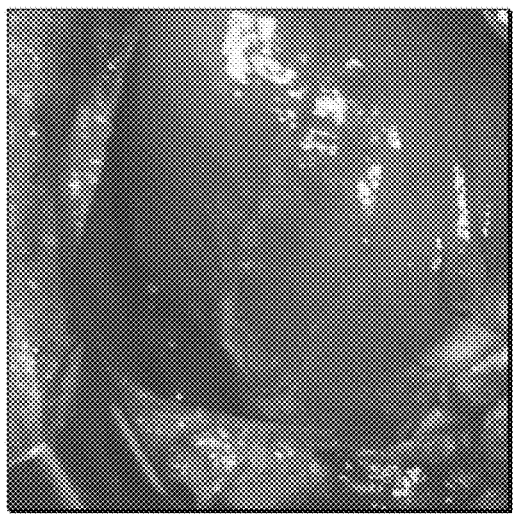
Figure 13D:
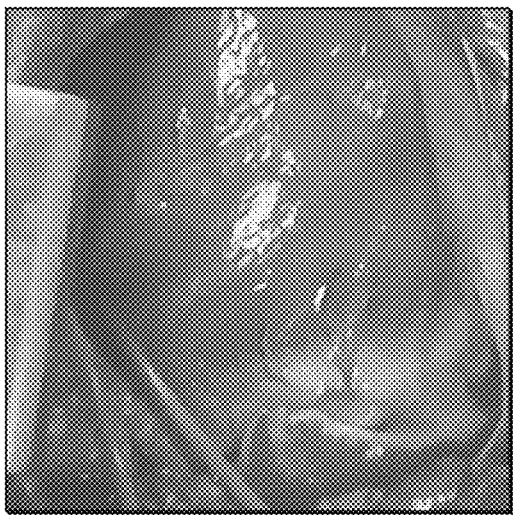

Referring now to FIGS. 13A-13D, images illustrating Panel A, an NIR 785 nm image of a pig heart (13A); Panel B, Green 532 nm image of the same pig heart (13B); Panel C, a reconstructed color image of the same pig heart (13C); and Panel D, an image of the same pig heart taken by a regular camera (13D) will be discussed. FIGS. 13A-13D illustrate using an NIR image as a red color channel and a 532 nm image as a green color channel, the color image of a pig heart can be generated without using a color camera. If the information of one color channel is missing, an algorithm is designed to generate this data using the information of the other two color channels. Since the color of a sample (tissue/organ) is mainly red, embodiments of the present inventive concept can generate color that is very close to the original one as long as the information of the red color channel is available as discussed with respect to FIGS. 10A-10D and 11A-11D. Thus, embodiments of the present inventive concept allow the reconstructed color image to reveal information of deeper tissue/organ if NIR is used as the red color channel as shown in Panel C (FIG. 12C) vs. Panel D (FIG. 12D).

As discussed briefly above with respect to the Figures, some embodiments of the present inventive concept use two wavelengths of differential transmittance through target tissue to apply LSI or LDI. In some embodiments, a first wavelength is within the visible range having zero or very shallow penetration, such as blue light (450-495 nm). The imaging result of this non-penetrating illumination serves as capturing the anatomical structure of tissue/organ surface and position marker of the target tissue/organ, but not the subsurface movement of blood flow and perfusion. A second of the two wavelengths is Near Infra-Red (NIR), which has much deeper penetration and the imaging result of this NIR illumination reveals the underlying blood flow physiology, which correlates both to the motion of the target tissue/organ and also the movement of blood flow and perfusion.

Using the imaging measurement of the visible light as a baseline, the true motion of blood flow and perfusion can be derived from the NIR imaging measurement without being affected by the motion artifact of the target. Furthermore, the anatomical structure information captured by visible light and the physiological characteristics measured by NIR light may be synthesized together according to some embodiments of the present inventive concept. The synthesized imaging product according to embodiments discussed herein provides a previously unattainable clarity of visualization and accuracy of quantification of blood flow and perfusion across the spectrum of clinical applications of laser imaging technologies.

Thus, embodiments of the present inventive concept provide improved image quality and real time data acquisition (several seconds vs. minutes for all other technologies) and analysis. This real time aspect of the present inventive concept makes this technology a real option for sustained adoption of the technology by a surgeon/provider. Embodiments of the present inventive concept accurately depict and quantify blood flow and perfusion.

Further embodiments of the present inventive concept are directed to color image reconstruction using multi-wavelength imaging techniques discussed herein. It will be understood that the images are presented in a gray scale as the patent application publishes in black and white. In particular, using a dual wavelength imaging technique as discussed herein, two images may be acquired simultaneously. One is near infra-red image IR(x, y) and the other is a visible image VIS(x, y). X and Y represent the index of the horizontal and vertical pixel. To reconstruct a red green blue (RGB) color image, red, green and blue channels are calculated separately as follows:

$$R(x, y) = (2^N - 1) \times a_1 \times \left(\frac{NIR(x, y) - \min(NIR(x, y))}{\max(NIR(x, y)) - \min(NIR(x, y))}\right)^{b_1} \quad \text{Eqn. (5)}$$

$$G(x, y) = (2^N - 1) \times a_2 \times \left(\frac{VIS(x, y) - \min(VIS(x, y))}{\max(VIS(x, y)) - \min(VIS(x, y))}\right)^{b_2} \quad \text{Eqn. (6)}$$

$$B(x, y) = (2^N - 1) \times a_3 \times \left(\frac{VIS(x, y) - \min(VIS(x, y))}{\max(VIS(x, y)) - \min(VIS(x, y))}\right)^{b_3} \quad \text{Eqn. (7)}$$

$$\frac{NIR(x, y) - \min(NIR(x, y))}{\max(NIR(x, y)) - \min(NIR(x, y))} \quad \text{Eqn. (8)}$$

where R(x,y), G(x,y), B(x,y) are the red, green and blue channels, respectively, of the RGB color image; N is the bit of the color map, for example, 8 bit or 16 bit; a and b are the adjusting parameters for each channel; min is the function to get the minimum value; max is the function to get the maximum value; and Eqn. (8) serves as a normalization of the original image of one specific wavelength. Furthermore, the brightness, contrast and gamma value of the original image of one specific wavelength might be adjusted before applying the equations above.

The multi-wavelength color image recreation technique in accordance with some embodiments of the present inventive concept may reduce the need for an extra color camera in the device; can create a color image with a minimum of two wavelengths; and compared with traditional color images, the color image produced in accordance with embodiments discussed herein visualizes a larger depth of penetration due to use of near infra-red wavelength.

Figure 14A:
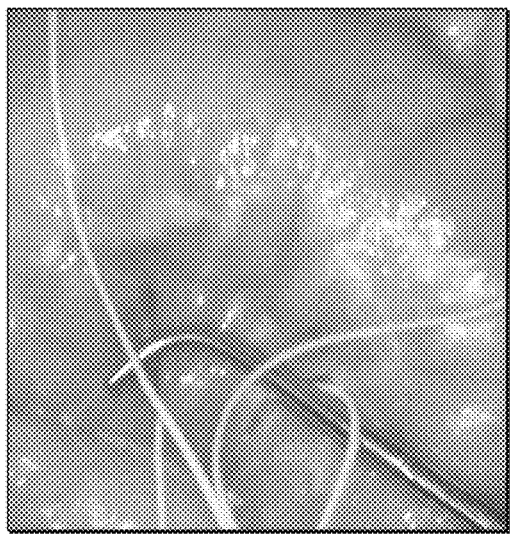
Figure 14B:
Figure 14C:
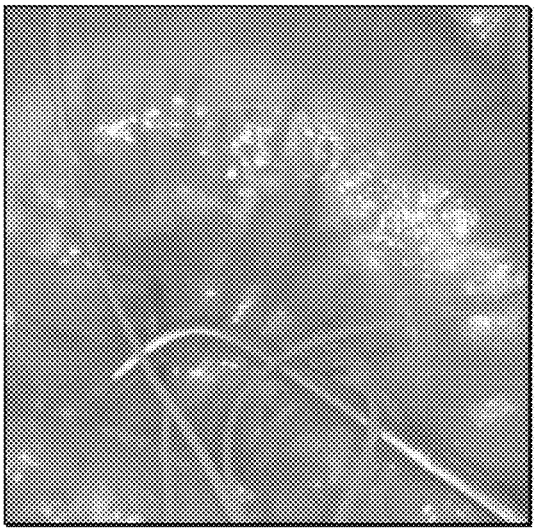
Figure 14D:
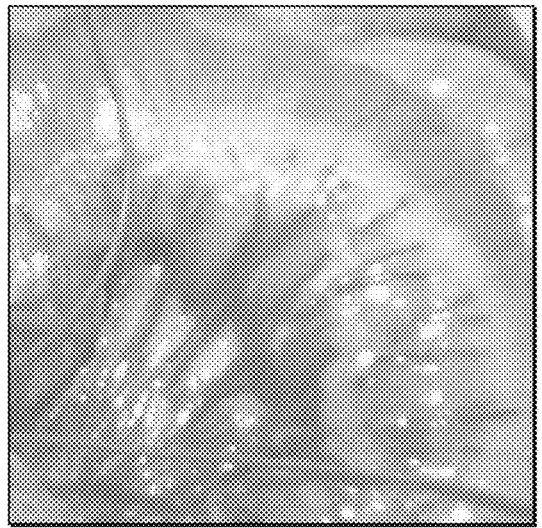

Referring now to FIGS. 14A through 14E, various images of a segment of a large bowel of a pig imaged using the multi-wavelength imaging device in accordance with some embodiments of the present inventive concept will be discussed. FIG. 14A is an image of the bowel of the pig obtained using a visible wavelength (532 nm). FIG. 14B is an image of the bowel of the pig using a near infra-red wavelength (785 nm). FIG. 14C is an image of the bowel of the pig reconstructed with the wavelengths of FIGS. 14A and 14B. FIG. 14D is a regular color image (shown in gray scale) of the bowel with room light illumination. FIG. 14E is a blood flow and perfusion image of the bowel in accordance with some embodiments of the present inventive concept.

Referring now to FIGS. 15A to 19B, details with respect to real time image quality test protocols will be discussed. Real time image quality test protocols are developed based on customized algorithms using image registration and image metadata to examine the following issues during a clinical imaging procedure:

Movement of target: FIGS. 15A and 15B illustrate images of a stationary hand (15A) and a moving hand (15B) detected by a customized image registration algorithm. By a customized image registration and optical flow algorithm, the quantified detection result curves can be drawn under the images.

Movement of a field of view or the Camera: FIGS. 16A and 16B illustrate imaging of a hand image captured by stationary camera (16A) and a hand captured by moving camera (16B) detected by customized image registration algorithm.

Figure 17A:
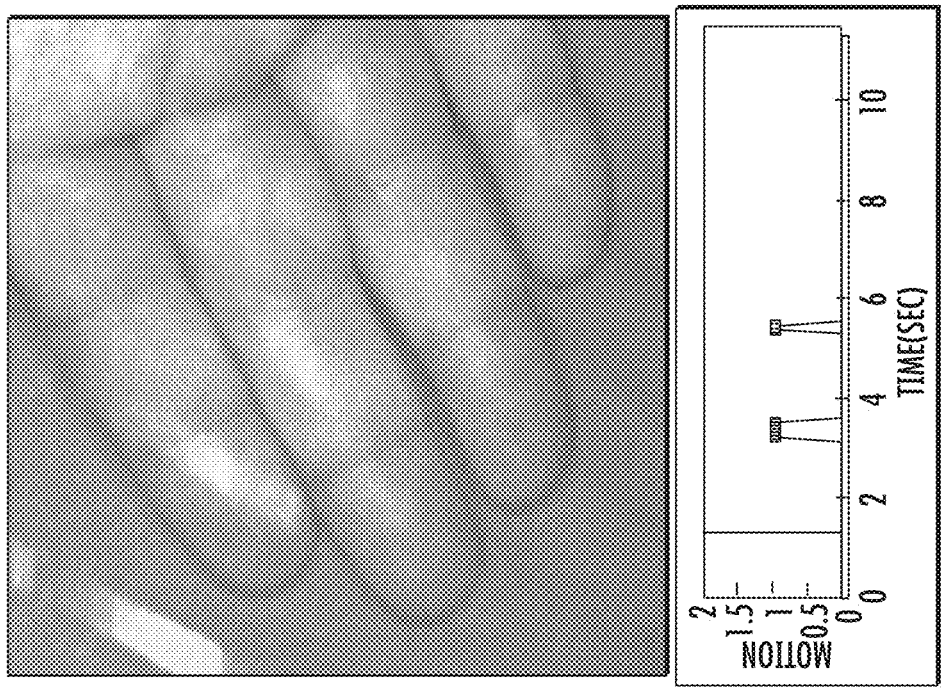
Figure 17B:
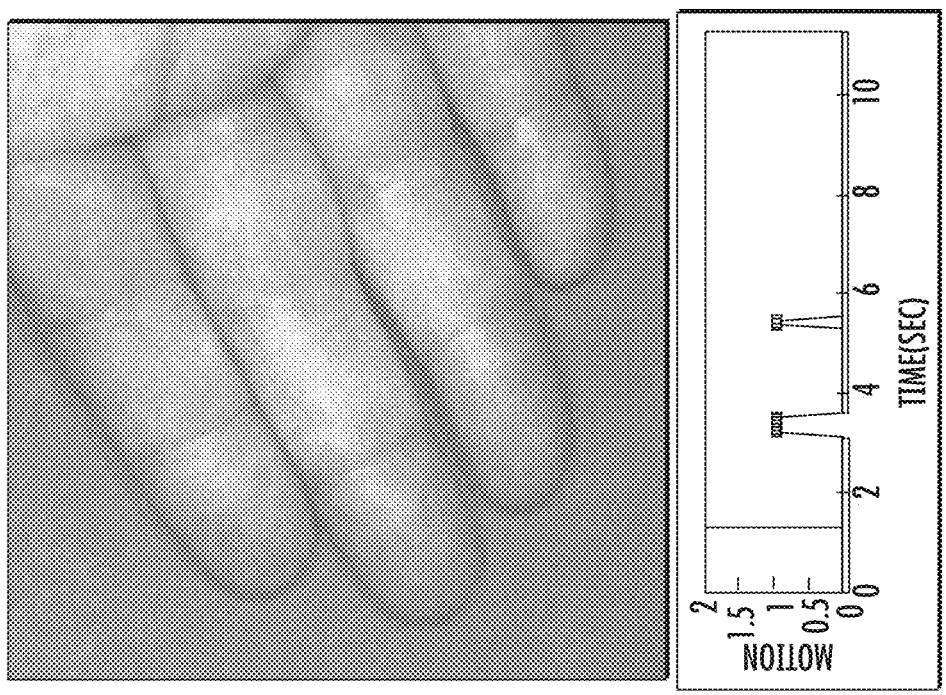

Blocked field of view: FIGS. 17A and 17B illustrate an image of a hand (17A) and an image of a hand that is partially blocked by a twister (17B) and this blocked field of view is detected by a customized image registration algorithm.

Intrusion of headlight of surgeon/physician: FIGS. 18A and 18B illustrate an image of a hand (18A) and an image of a hand with a head light shining on it (18B) and this extra light within the FOV is detected by a customized algorithm using metadata in the image.

Ambient light condition: FIGS. 19A and 19B illustrate an image of a hand with a room light off (19A) and an image of a hand image with the room light on (19B) and this is detected by customized algorithm using metadata in the image.

The goal of this process is to reduce the likelihood, or possibly eliminate, low quality images caused by incorrect image acquisition to improve the visualization and increase accuracy of the quantification of the blood flow and perfusion imaging in accordance with some embodiments of the present inventive concept.

As discussed above, the data obtained using the imaging methods discussed above can only be used to derive distribution of blood flow speed u. In clinics, the information on distribution of blood flow rate given by the product of blood flow velocity u and the cross section area of blood vessel A is needed. To obtain the distribution of u(r) where r is the three dimensional coordinate, the Navier-Stokes equation, has to be solved, which is given by Equations (9) and (10) set out below:

$$\rho \cdot \left( \frac{\partial u}{\partial t} + u \nabla \cdot u \right) = -\nabla p + \mu \cdot \nabla^2 u + F \quad \text{Eqn. (9)}$$

$$\frac{\partial \rho}{\partial t} + \nabla \cdot (\rho u) = 0 \quad \text{Eqn. (10)}$$

where $\rho$ is the density (kg/m$^3$), u is the flow velocity vector (m/s), p is the pressure (N/m$^2$ or Pascal), F is the volume force vector (N/m$^3$) and $\mu$ is the viscosity. Solving the Navier-Stokes equations produces a velocity field, i.e. a distribution of fluid velocity in space and time. Once this velocity field is obtained, other quantities of interest, such as flow rate and drag force, can be calculated. These calculated quantities can be compared to the experimental data obtained using the methods discussed above to validate the data.

Computational procedures for a non-invasive measurement of blood flow rate distribution in principal vessels in tissues/organs will now be discussed with respect to some embodiments of the present inventive concept. Procedures begin by illuminating a tissue region of interest with a coherent light source, such as a laser with sufficiently long wavelength for relatively large penetration depth between, for example, 550 nm to about 1100 nm as the second wavelength. Using methods discussed above, scattered light at the second wavelength is acquired to determine spatial distribution of blood flow speed in the principal vessels and perfusion distribution in tissue in the region of interest. A velocity field of u(r) for the region of interest is calculated numerically. In some embodiments, the velocity field is calculated using Equations (9) and (10) set out above. Blood flow speed in the region of interest based on the calculated velocity field is calculated. The calculated blood flow speed in the region of interest is compared to the blood flow speed determined using the acquired image data at the second wavelength from the region of interest to verify results.

As used herein, "blood flow rate distribution" refers to a relation between velocity distribution of u (the velocity vector, in m/sec) in the region of interest or field of view (FOV) and the blood flow distribution. Calculation of blood flow rate distribution (volume flow in cc/min) involves using tools such as computational fluid dynamics models to obtain blood flow rate (a surface integral of the u vector over the cross section of a vessel) from a measured distribution of velocity u. Furthermore, embodiments of the present inventive concept are configured for macro FOVs of, for example, about 100 mm×about 100 mm. Details with respect to FOV for various embodiments of the present inventive concept are discussed further below with respect to FIG. 31.

Figure 21A:
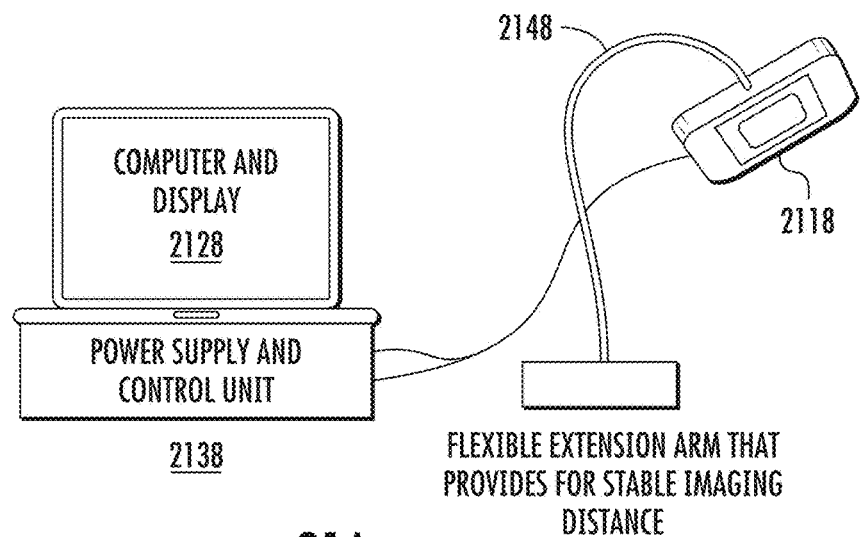
FIGS. 21A and 21B are diagrams illustrating a smaller footprint system in accordance with some embodiments of the present inventive concept.
Figure 21B:
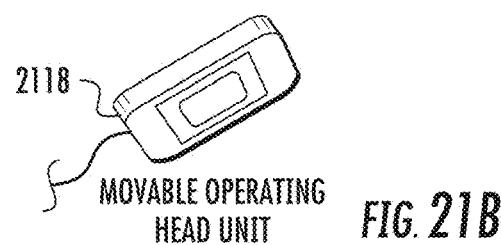

Referring now to FIGS. 20, 21A and 21B, various embodiments of non-invasive systems in accordance with embodiments of the present inventive concept will be discussed. Referring to FIG. 20, a mobile system in accordance with embodiments of the present inventive concept will be discussed. As illustrated therein, the system includes a mobile cart 2017 including, for example, a communications device (computer tower) 2027, a control box 2037, a series of shelves in a housing etc., and a computer terminal or display 2047 thereon; an extension arm 2057 and an operating head module 2067 in accordance with embodiments discussed herein. The mobile cart 2017 may include wheels 2018 and a mechanism for locking the wheels, for example, a brake, when the mobile cart 2017 is positioned near the subject. The operating head module may include a housing, a user interface, lights and alarms and the like without departing from the scope of the present inventive concept. The extension arm 2057 may be used to position the operating head module 2067 over the patient/subject 2077. The ability to move the system to the patient, rather than bring the patient to the system provides many advantages, especially for immobile patients. In some embodiments, the extension arm 2057 can including a plurality of articulating arm segments 2057s.

Referring now to FIGS. 21A and 21B, smaller footprint embodiments in accordance with inventive concept will be discussed. As illustrated in FIGS. 21A and 21B, a smaller footprint operating head unit may be used to provide operations in accordance with embodiments discussed herein. These systems may include a communications device 2128 including a computer console and related display and user interface, a power supply and a control unit 2138 all coupled to a handheld operating head unit 2118. As illustrated in FIG. 21A, in some embodiments the smaller footprint mobile operating head unit 2118 is coupled to the communications device 2128 using a flexible extension arm 2148. The flexible extension arm 2148 may allow the mobile operating head unit 2118 to be positioned on the target region of the patient/subject without repositioning the patient subject. FIG. 21B illustrates a mobile operating head unit 2118 without a flexible extension arm 2148. It will be understood that FIGS. 21A and 21B are provided as examples only and, therefore, embodiments of the present inventive concept are not limited to this configuration.

Figure 22:
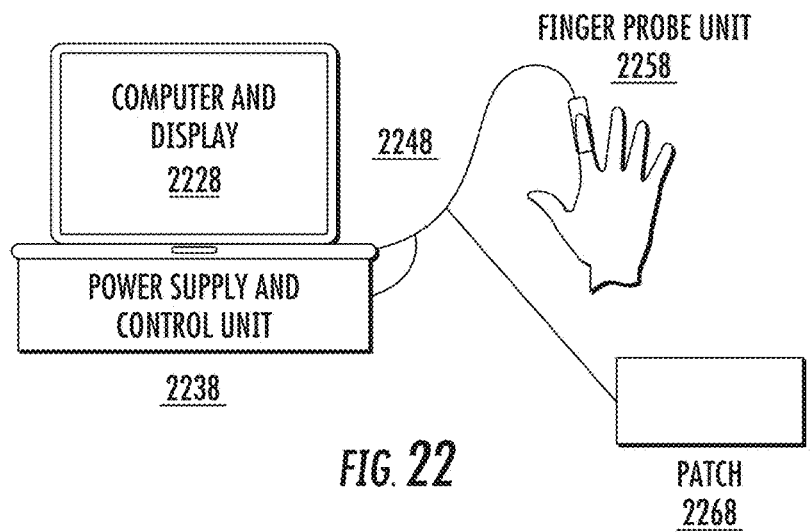
FIG. 22 is a diagram illustrating a finger probe device and/or skin patch in accordance with some embodiments of the present inventive concept.

Referring now to FIG. 22, finger probe/skin patch embodiments of the inventive concept will now be discussed. As illustrated in FIG. 22, these systems may include a communications device 2228 including a computer console and related display and user interface, a power supply and a control unit 2238 all coupled to a finger probe unit 2258 and/or a skin patch 2268. As illustrated in FIG. 22, in some embodiments the finger probe unit 2258 or the skin patch 2268 is coupled to the communications device 2228 using a flexible extension arm and/or cable 2248. The flexible extension arm 2248 allows the finger probe unit 2258 and/or the skin patch 2268 to be positioned on a finger or skin of the subject without repositioning the subject. It will be understood that FIG. 22 is provided as an example only and, therefore, embodiments of the present inventive concept are not limited to this configuration.

Figure 23:
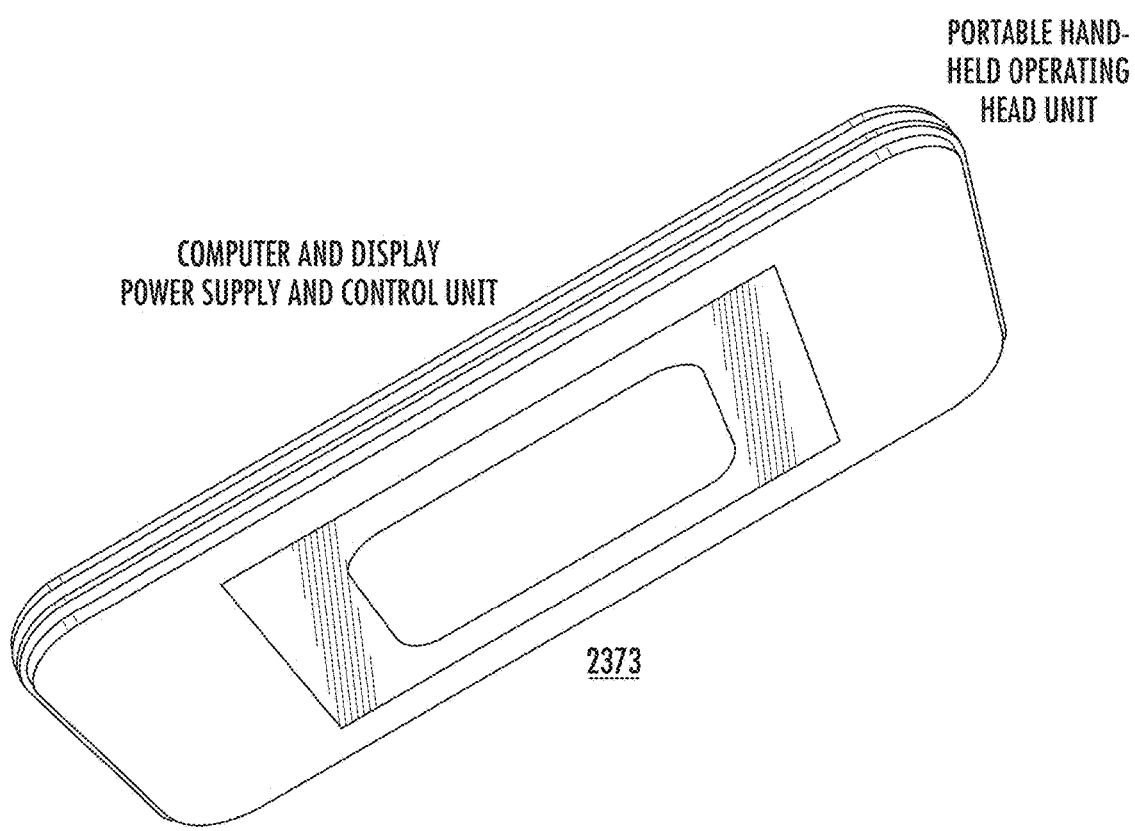
FIG. 23 is a side perspective view of a handheld mobile system in accordance with some embodiments of the present inventive concept.

Referring now to FIG. 23, hand-held mobile embodiments of the present inventive concept will now be discussed. As illustrated in FIG. 23, these systems may include a communications device 2373 including, for example, a microchip computer and related display and user interface (as shown in FIG. 21A), a battery power supply and a control unit. The image is captured non-invasively at a focused distance or by contact with a surface of the handheld unit. Embodiments may include image capture, analysis, display and storage as discussed above. Wireless communication protocols may be used to download the stored information without departing from the scope of the present inventive concept.

As is clear from details discussed herein and FIGS. 20 through 23, there are common components that are included in the various embodiments and form factors discussed herein. In particular, the system generally includes optics including a camera that can be a customized multi-sensor device; multiple near infrared and visible lasers; a light emitting device (LED) (for example, 2410, FIG. 24) to locate a field of view (FOV); distance sensors to mark the distance to ensure the appropriate size of the field of view; and fiber and other front end optics.

Most embodiments include a communications device, i.e. a computer and display unit to process the raw image from the camera and visualize the blood flow and perfusion in tissue/organ and communicate with the electronic control board.

The systems are coupled to a power supply and a control unit or any combination thereof. For example, an alternating current (AC), direct current (DC) or battery power supply provides power for different components in the system. Furthermore, an electronic control board can control different components and read feedback and communicate with the computer through software.

Some embodiments of the present inventive concept provide real time software analysis and visualization to provide simultaneous anatomical and blood flow and perfusion physiological views as illustrated, for example, in FIGS. 26A through 26D. It will be understood that for each embodiment (form factor) the key components and output may vary without departing from the scope of the present inventive concept. For example, in the finger probe application (FIG. 22), the numbers and measurement curve will be used instead of image data.

Figure 26A:
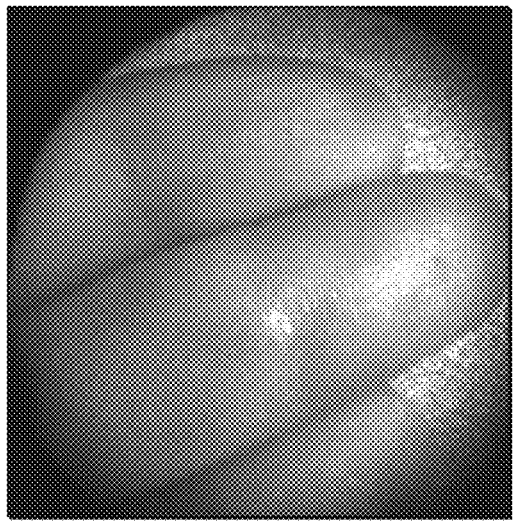
FIGS. 26A through 26D are images of a human hand captured in accordance with embodiments of the present inventive concept.
Figure 26B:
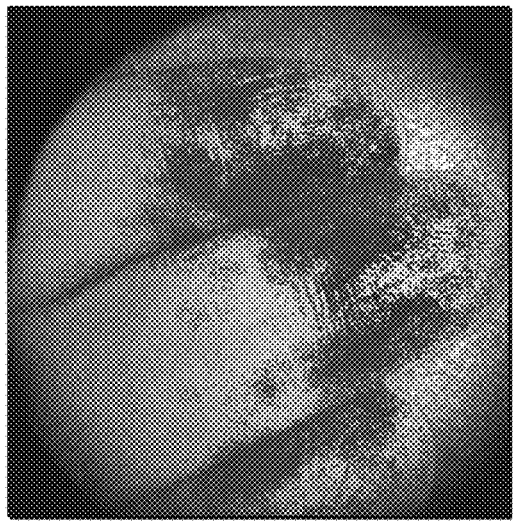
Figure 26C:
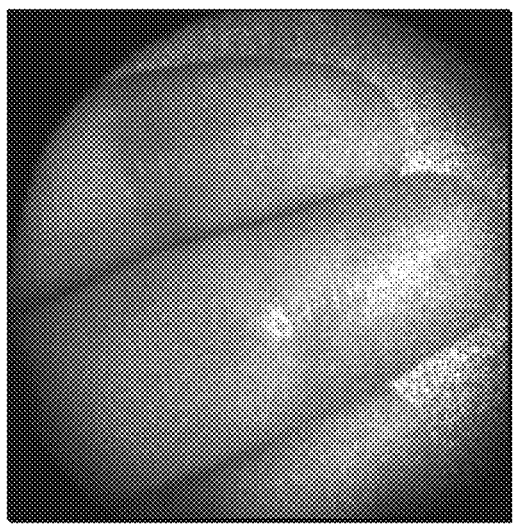
Figure 26D:
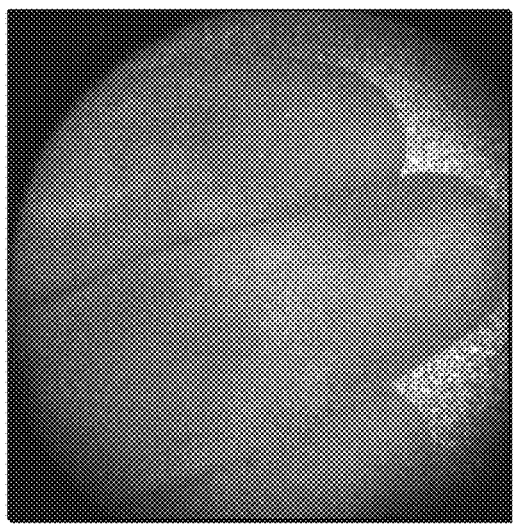

Referring now to FIGS. 26A through 26D, images obtained using methods and systems in accordance with embodiments discussed herein will be discussed. FIGS. 26A and 26B are an anatomical view and a blood flow physiology of a normal human hand, respectively. FIGS. 26C and 26D are an anatomical view and a blood flow physiology of an abnormal human hand with insufficient blood supply, respectively.

As discussed above, some embodiments of the present inventive concept provide methods, systems and computer program products for non-invasive determination of blood flow and perfusion in a sample. Although multi-spectral physiologic visualization (MSPV) can be used in a non-invasive, open surgical setting with direct illumination of the tissues, embodiments of the present inventive concept are not limited to this configuration. In particular, recently many surgical procedures have been performed using endoscopy-based illumination for visual access within cavities of the body. According to some embodiments of the present inventive concept, MSPV can be adapted for an endoscopic platform, which includes, for example, endoscopic cavitary surgery, minimally invasive surgery, and robotic surgery, all of which use endoscopic visualization to illuminate the tissues and organs and to perform the procedure as will be discussed further herein.

As used herein, an "endoscopic system" refers to both an endoscope-type device or placement of an endoscope-type device into a cavity, recess, natural lumen or tube-like structure in the subject, for example, the human body.

Figure 24:
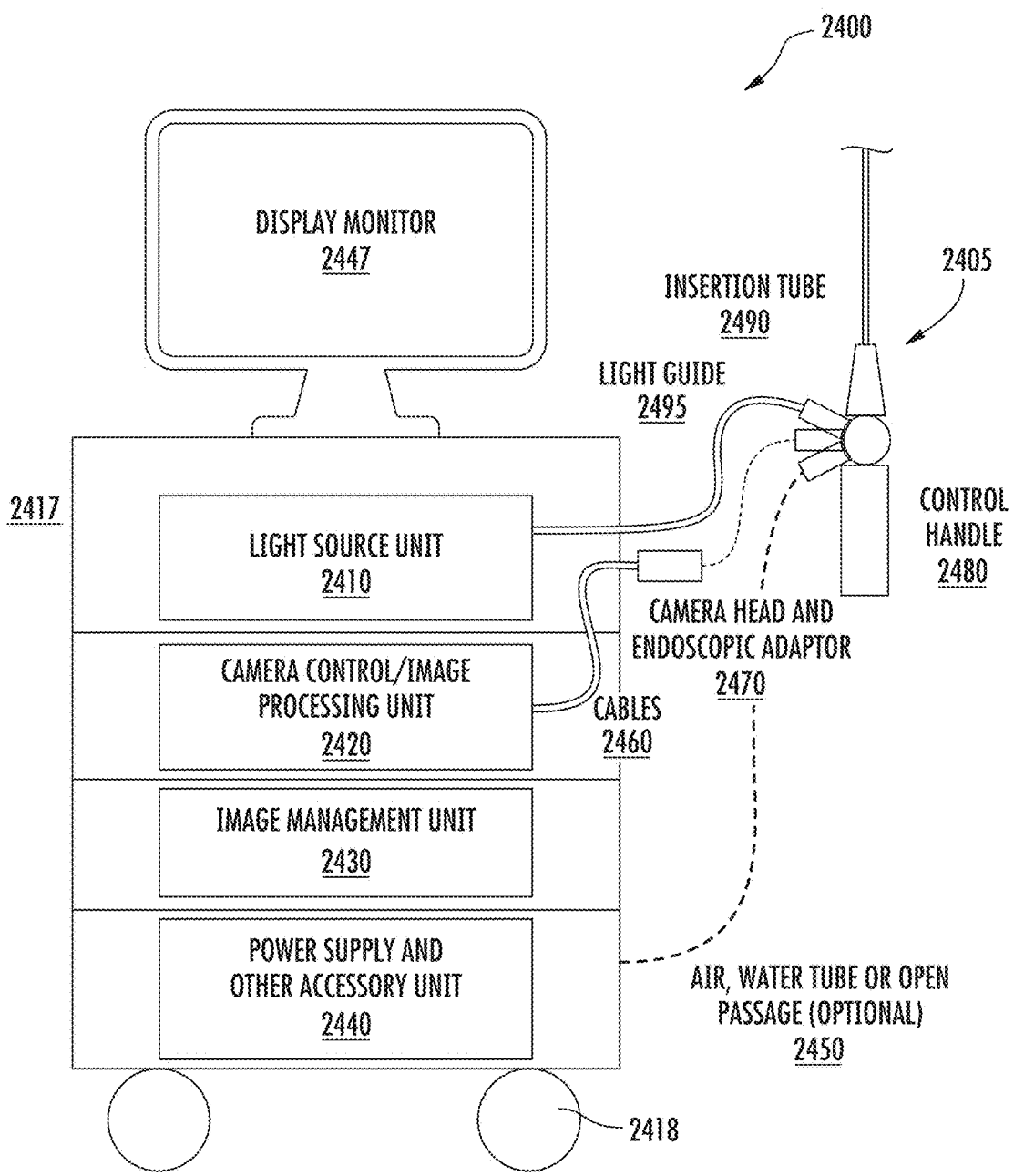
FIG. 24 is a diagram of a standalone system including an endoscopic device in accordance with some embodiments of the present inventive concept.

Referring now to FIG. 24, a standalone MSVP endoscopic system 2400 including an endoscopic device 2405 in accordance with some embodiments of the present inventive concept will be discussed. As will be discussed further below with respect to FIG. 25, embodiments of the present inventive concept are not limited to standalone systems. Referring to FIG. 24, the system includes a mobile cart 2417 including, for example, a light source 2410; a camera control and image processing unit 2420; an image management unit 2430; a power supply and other accessory unit 2440; a display 2447 and an endoscopy device 2405 coupled thereto in accordance with some embodiments discussed herein.

The endoscopy device 2405 includes a light guide 2495 coupled to the light source 2410, a camera head and endoscopic adapter 2470 coupled to the camera control 2420 and an optional air and water tube 2450 coupled to the accessory unit 2440. The light guide 2495, the camera head and endoscopic adapter 2470 and the air and water tube 2450 may be connected to a control handle 2480 of an insertion tube by cables 2460. The insertion tube may be flexible, semi-rigid or rigid as will be discussed below.

The mobile cart 2417 may include wheels 2418 and a mechanism for locking the wheels, for example, a brake, when the mobile cart 2417 is positioned near the subject. The mobile cart 2417 may also include shelving etc. for the various equipment modules included therein. Although embodiments of the present invention are illustrated in FIG. 24 as being a mobile cart, it will be understood that embodiments of the present inventive concept are not limited to this configuration. For example, the equipment may be stationary or embedded within a larger integrated system (e.g., Operating Room suite systems) without departing from the scope of the present inventive concept. However, the ability to move the system to the patient, rather than bring the patient to the system provides many advantages, especially for immobile patients.

Details of the system illustrated in FIG. 24 will now be discussed. As discussed above, some embodiments include a mobile cart 2417, which can be used to transport the whole endoscopic system into different units of the hospital or clinic area. Brakes can usually be applied when the system needs to be secured. Multiple shelves, brackets and holders may be designed to contain different modules, mount monitor and hold the endoscope and accessories.

The display monitor 2447 is not limited to the single monitor shown in FIG. 24. For example, one or more monitors may be provided on the mobile cart 2417 without departing from the scope of the present inventive concept. The monitor(s) 2447 may connect to the camera control and image processing unit 2420 to be viewed by, for example, physicians or nurses, in real time. The monitor(s) 2447 may also connect to the image management unit 2430 to be viewed for case and episode management. In further embodiments, the monitor 2447 may be provided on the display on the endoscope itself. In some embodiments, an adapter mat be provided in the system that allows the system to be connected to existing monitors in the operating room (OR).

The light source 2410 may include a multi-spectral LED light to guide the field of view (FOV) of the endoscope insertion process. The light source 2410 may also include one or more multi-spectral lasers for blood flow and perfusion visualization once the region of interest (ROI) is located. The light source unit 2410 is generally connected to the endoscope with optic fibers. Embodiments of the present inventive concept may provide a light source 2410 specifically configured to work in endoscopic environments.

The camera control and image processing unit 2420 receives image data from the camera sensors that are located in the endoscope. An embedded processing system (different from PC) will process the raw data using algorithms and the multi-spectral perfusion visualization (MPSV) and regular color visualization will be sent to the display monitor 2447. The embedded processing system may also control the camera sensors in the endoscope and adjust the camera settings. In some embodiments, the camera head 2470 (or part of the camera head) can be located in the camera control and image processing unit to reduce the profile of the endoscope. In some embodiments, the camera is specifically designed for endoscopic environments accordance with those discussed herein.

The image management unit 2430 may be configured to provide a user interface for case and episode management; image file management, for example, data archiving and exporting; and other system management such as network connectivity. The image management unit 2430 may be achieved by a PC-style architecture with, for example, a Windows or LINUX operating system. It will be understood that the image management unit can be incorporated into the camera control and image processing unit 2420 to make the endoscopic system more compact without departing from the scope of the present inventive concept. However, the two units may also remain separate.

The power supply 2440 is physically isolated from the electrical plug for safety reasons. The other accessories such as water, air supply and suction pump etc. may be needed depending on the specific clinical application.

The endoscope 2405 is provided by the insertion tube 2490, the light guide 2495, the camera head and endoscopic adapter 2470, the cables 2460, the optional air, water, or open passage tubes 2450 (dotted lines indicate the optional elements) and the control and handle 2480. It will be understood that in some embodiments, flexible scopes may have air, water, and open passage (e.g., a biopsy channel) and may not have one or more of these elements in another embodiments. Rigid scopes may have an open channel, but may not have not air/water. For laparoscopic/thoracoscopic/robotic endoscopes, there are typically no channels in the rigid scopes.

Details of these elements of the endoscopic system 2400 will now be discussed. Some embodiments provide two type of insertion tubes 2490, rigid and flexible. It will be understood that in some embodiments the insertion tube could be semi-rigid without departing from the scope of the present inventive concept. Each contains an optical lens and/or fiber bundles to illuminate the target with LED and near infrared laser light and receive light that is reflected from the target. The insertion tube may also include water, air and suction channels depending on the specific clinical application.

A flexible insertion tube may, for example, include a light guide connector, a light guide tube, video remote switches, a control body, a bending section of the insertion tube which may include internal instrument channels. A rigid endoscope may include, for example, an eyepiece, an eyepiece sleeve, fiber optics, a fiber guide, a light cone and sleeve, a light post and rigid insertion tube with a distal tip. At an end of the rigid insertion tube an objective lens assembly may be provided.

Referring again to FIG. 24, the light guide 2495 is plugged into the light source unit to transmit light. The camera head can be potentially located in, for example, an endoscopic adapter 2470. The image may be carried from the distal tip of the endoscope to the camera head by lens and/or fiber bundles and then electronically transferred to the camera control and image processing unit 2420 through cable 2460.

The camera head (or part of the camera head) 2470 can be potentially located in the camera control and image processing unit 2420 to reduce the profile of the endoscope.

An image can be formed at the distal tip of the endoscope and/or image data can be obtained using image sensors (S1-SN—FIG. 1C) and transmitted electronically to the camera control and image processing unit 2420. Different control buttons are located around the handle 2480 of the endoscope to achieve field of view and imaging control etc. during the operation procedure. For example, in some embodiments, the sensors S1-SN (FIG. 1C) may be arranged along a continuum from the tip of the endoscope to a distance remote from the endoscope coupled by image capture cabling.

Figure 25:
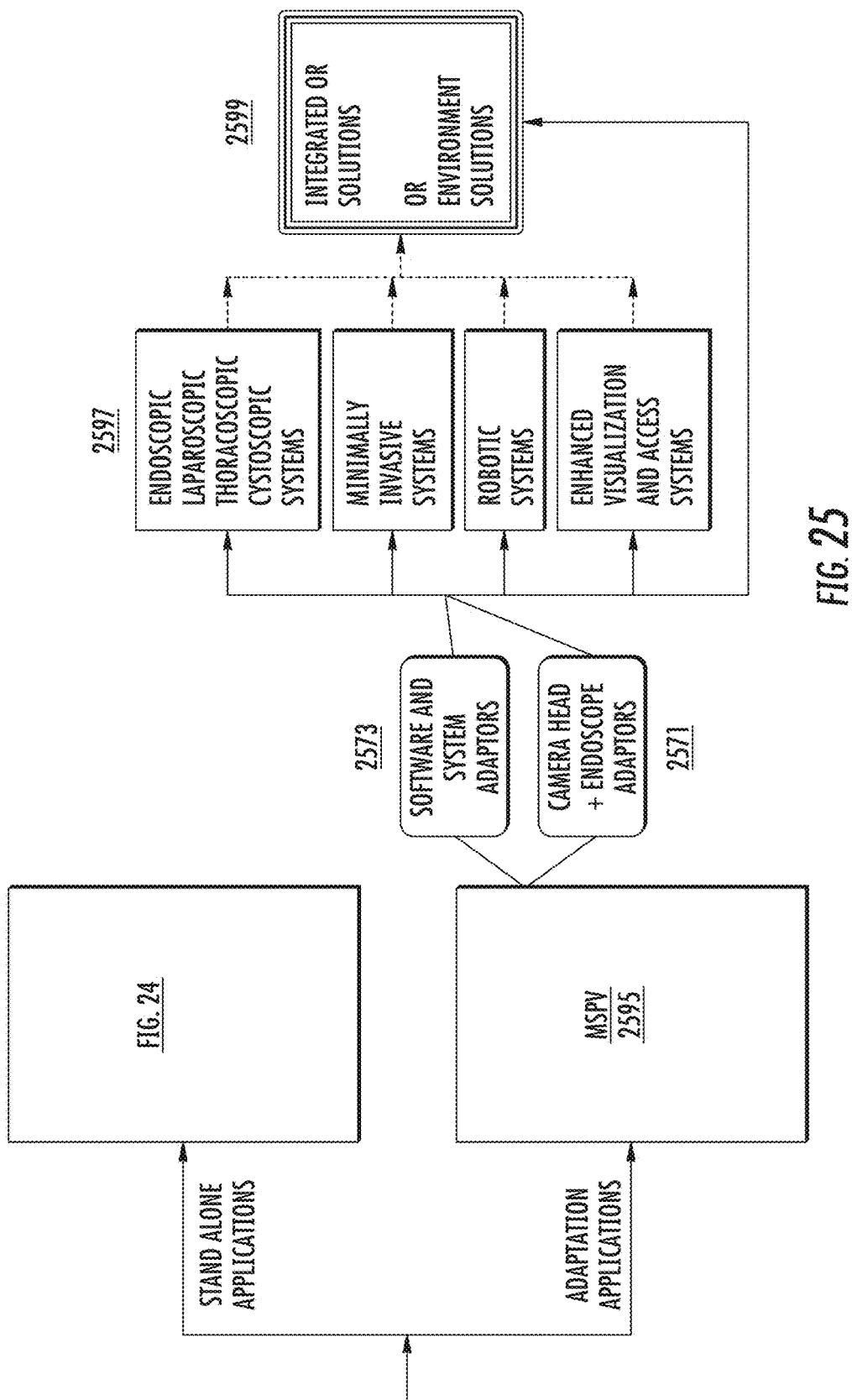
FIG. 25 is a block diagram of an adaptive system in accordance with some embodiments of the present inventive concept.

Referring now to FIG. 25, as discussed above, embodiments of the present inventive concept are not limited to a standalone system discussed with respect to FIG. 24. FIG. 25 is a block diagram illustrating both a standalone system and adapted system. The standalone system illustrated in FIG. 25 is similar to the standalone systems—illustrated and discussed with respect to FIG. 24. Accordingly, the details will not be repeated herein in the interest of brevity.

When the adaptation applications are used, the MSVP system 2595 interfaces with a camera head and endoscopic adapters 2571. Software applications 2573 are provided interface with system adapters and system software. Both the hardware 2571 and the software 2573 of the adaptive system can be connected to any system 2579, for example, endoscopic systems, thoracoscopic systems, minimally invasive systems, robotic systems, enhanced visualization and access systems, and the like. Thus, existing systems can use the inventive concept discussed herein. In further embodiments, the existing systems can be interfaced into Integrated OR systems (OR Environment Solutions) 2599. It will be understood that embodiments of the present inventive concept are not limited to embodiments illustrated in FIG. 25, which is provided for example only. For example, blocks illustrated in FIG. 25 may be combined or expanded without departing from the scope of the present inventive concept. For example, although block 2753 is illustrated as having three functions, these functions can be separated into two or more blocks.

Figure 27:
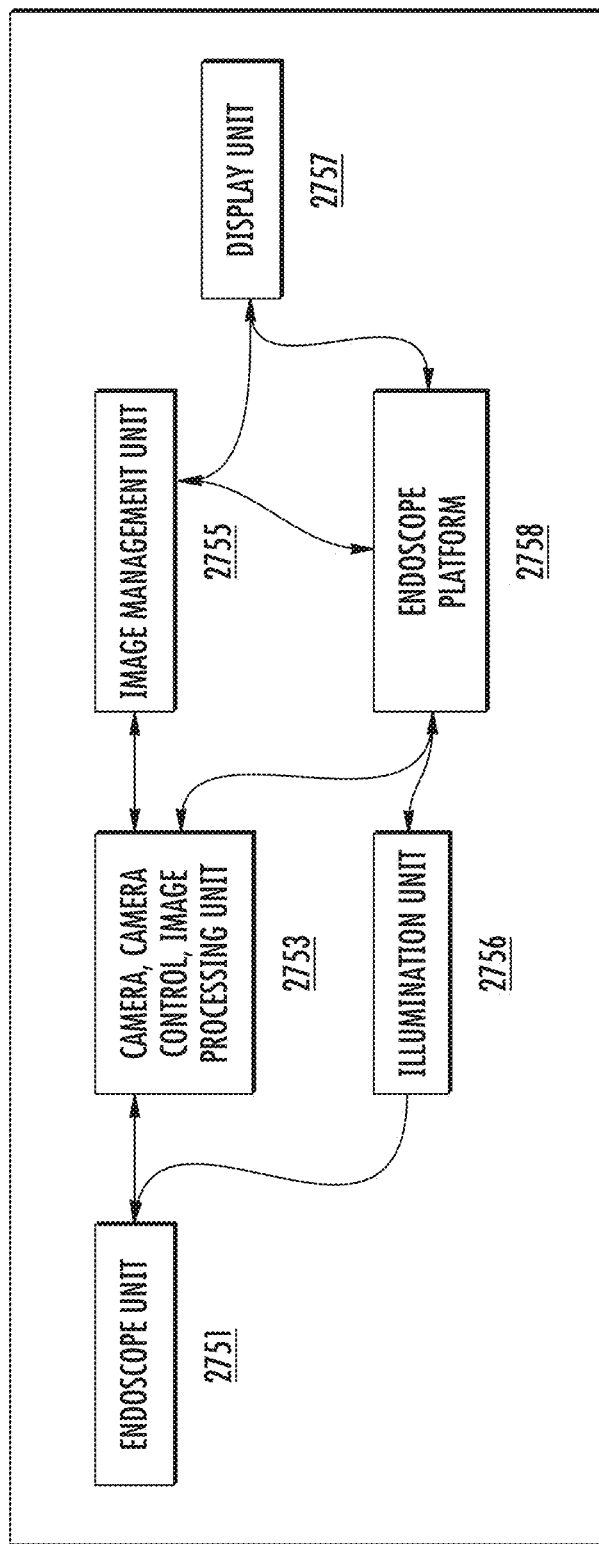
FIG. 27 is a block diagram of a system including an endoscope in accordance with various embodiments of the present inventive concept.

A block diagram of an endoscopic system in accordance with some embodiments of the present inventive concept is illustrated in FIG. 27. As shown, the endoscopic system includes an endoscopic unit 2751; a camera 2753; a camera control 2753; an image processing unit 2753; an illumination unit 2756; an image management unit 2755; an endoscopic platform 2758 and a display unit 2757. FIG. 27 is provided for example only and, thus, embodiments of the present inventive concept are not limited to this configuration. Units or modules may be combined or expanded into multiple units without departing from the scope of the present inventive concept.

In some embodiments, one or more cameras may be used. A single camera may have one or more sensors available.

In the adaptation of MPSV for an endoscopic application, several modifications are considered. The adapted endoscopic system components may include a modified endoscope technology, a camera, camera control and image processing unit, an image management unit, an operating system interface with the endoscopic platform operating system, and an interface with the endoscopic platform display(s).

In some embodiments, the illumination source is modified to accommodate the illumination path to include an endoscope In some embodiments, the illumination path is modified to produce a highly coherent beam. In further embodiments, this beam is diffused equally over the FOV, is focused at a certain distance, and provides high image quality and fidelity.

In still further embodiments the illumination source is multiple lasers, but can also include non-laser high-energy LEDs. Both laser and LED illumination may be used.

In some embodiments, the illumination light path travels from the source out to the target through the endoscope fiber array that consists of multiple wavelength-specific illumination fibers as well as image capture fibers.

In some embodiments, the camera is a miniaturized multi-sensor camera affixed to the endoscope. In other embodiments, the camera system is connected via cable to the endoscope. In these embodiments, the reflected and scattered light is captured by the camera with minimal loss through the fiber connectivity between the endoscope tip and the camera. In some of these embodiments, the camera will be a variable distance from the endoscope body to facilitate incorporation into existing endoscope-based platforms.

In some embodiments, the camera speed is about 150 frames per second to effect imaging fidelity and real-time analyses.

In some embodiments, the MSPV operational software (but not the MSPV image capture or the MSPV analysis software) will be integrated into the endoscope-based platform operational software in order to work seamlessly together. This interface with the endoscope-based platforms includes the platforms of endocavitary surgery such as laparoscopic surgery, thoracoscoic surgery and others inside a body cavity, minimally invasive surgery platforms such as minimally invasive Coronary Artery Bypass Graft surgery, and endoscope-based robotic surgical platforms.

In other embodiments, the image display quality is high definition (HD), three-dimensional (3-D), or four-dimensional (4D) and organic light emitting diode (OLED), all compatible with the MSPV analyses presentation.

In some embodiments the endoscope design is a rigid scope, with a straight or an angled lens at the tip.

In some embodiments the camera chip can be localized at the endoscope tip.

In some embodiments the endoscope design is a rigid scope with a flexible tip, where the camera chip and lenses are in the distal 2.0 cm of the 'rigid' scope; this distal 1.0 cm is flexible with a 360 degree radial field of view.

In some embodiments the scope is a flexible endoscope for endoscopic, bronchoscopic and similar 'scopic' procedures, incorporating this scope design modified technically to enable MSPV imaging and analysis in real-time.

Figure 28:
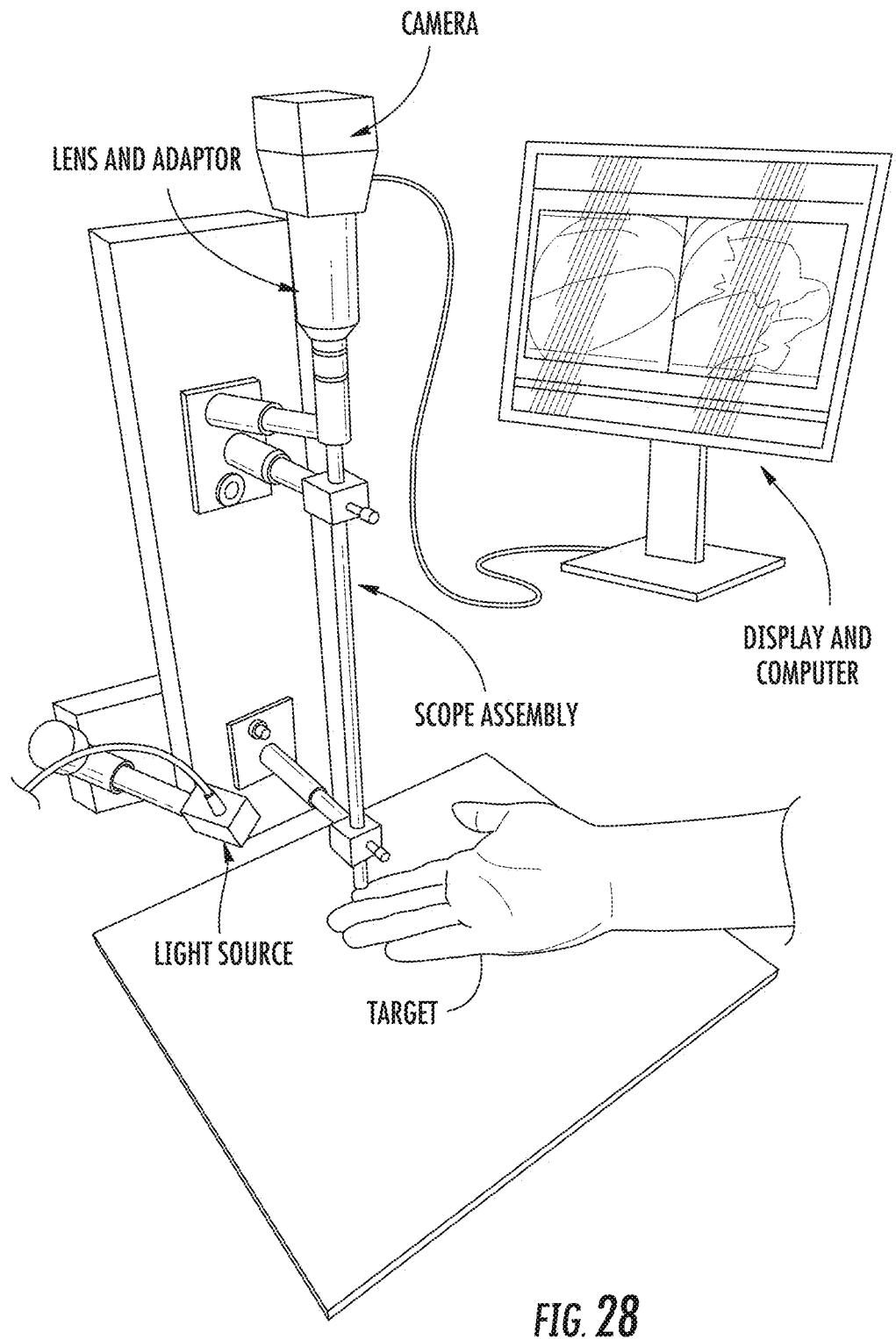
FIG. 28 is line drawing of an example system of FIG. 27 in accordance with some embodiments of the present inventive concept.

FIG. 28 is an example of an actual system in a lab including some or all of the components discussed above with respect to FIG. 27. Experiments have been performed using this system. The experiment setup of simultaneous reflectance imaging (illustrating anatomical structure) and near infrared laser speckle imaging (illustrating blood flow and perfusion distribution map) through a rigid laparoscope on optics bench top is illustrated in FIG. 28. This experiment can be accomplished with one or multiple wavelength illumination and imaging in real time. For example, in some embodiments, the light source shines one or multiple wavelength light with a homogenous beam profile on a target (fingers) and the diffused reflected light is imaged through a rigid endoscope, lens and adapter and imaged on a single sensor or multiple-sensor camera(s). The raw image data is transferred to the computer and processed using Eqns. 1 and 3 (for laser speckle imaging) and Eqns. 2 and 3 (for laser Doppler imaging). The anatomical structure and blood flow and perfusion distribution map are generated by algorithms discussed above with respect to FIGS. 10A-10D and Eqn. 4 and FIGS. 11A-11C and displayed on the monitor in real time as shown in FIG. 2. Note that in this experiment the illumination light is delivered outside the endoscope and in practice the illumination light (one wavelength or multiple wavelength) can be delivered through the endoscope (rigid or flexible) using fiber bundle, micro lens and diffuser. This experiment is provided for example only and is not intended to limit the scope of the inventive concept.

Figure 29A:
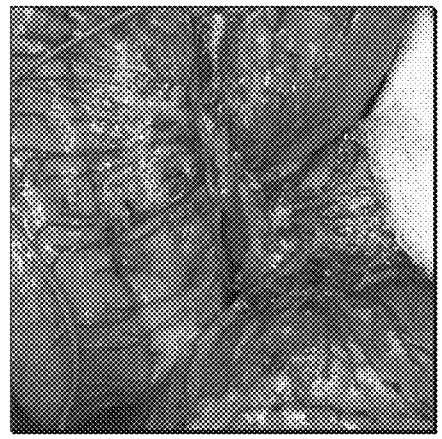
FIGS. 29A and 29B illustrate images and an image quality indicator bar used in a quality check method in accordance with some embodiments of the present inventive concept.
Figure 29B:
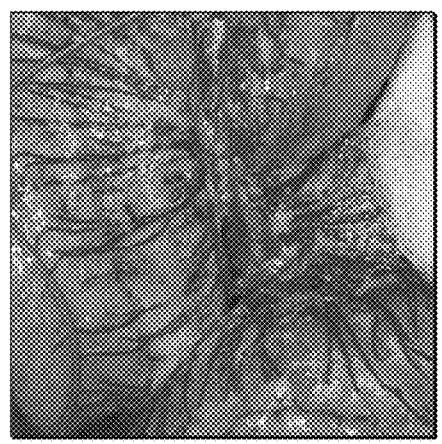

Referring now to the images and quality scale illustrated in FIGS. 29A and 29B. When MSPV videos, anatomical structure (FIG. 29A) and blood flow and perfusion distribution map (FIG. 29B) are displayed in real time or played back, a red (9-11); yellow (4-6); and green (0-4 and 6-9) colored time line bar (bottom) shown in black and white herein with numbers 0-11 can be used to indicate the time mark and the image quality at that time mark. The image quality checking results can be accomplished and embedded in the MSPV viewing section in real time or retrospectively in review mode without departing from the scope of the present inventive concept. In some embodiments, the image quality indicator bar is combined with the time line bar while the user is viewing the image in real time or retrospectively. The colors (red, yellow, green) or numbers 1-11 indicate the quality of video at that specific time mark. For example, green (0-4 and 6-9) may indicate a good quality image; yellow (4-6) may indicate a medium quality image and red (9-11) may indicate a poor quality image. Embodiments are not limited to the specific colors, numbers or scale illustrated in FIGS. 29A and 29B. Any scale can be used without departing from the scope of the present inventive concept.

Figure 30:
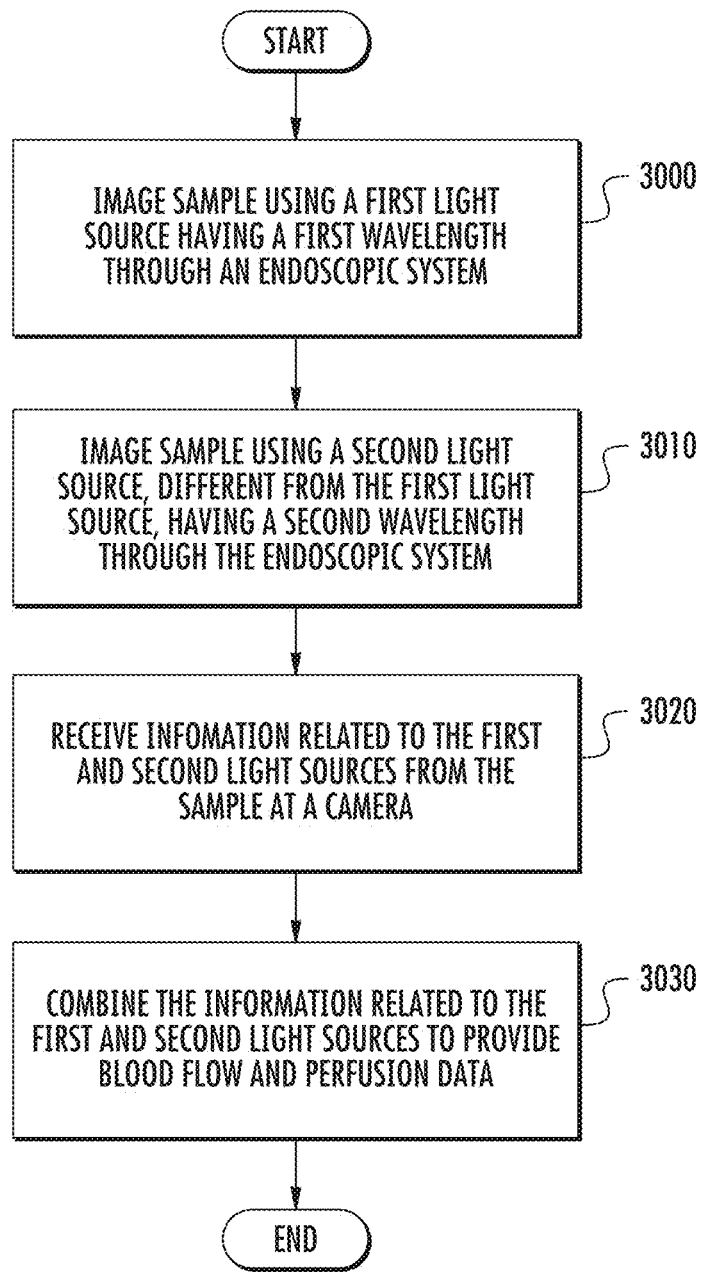
FIG. 30 is a flowchart illustrating methods in accordance with some embodiments of the present inventive concept.

Referring now to FIG. 30, a flowchart illustrating methods in accordance with some embodiments of the present inventive concept will be discussed. Operations for multispectral imaging in a multispectral imaging system adapted for an endoscopic system begin at block 3000 by imaging a sample using a first light source having a first wavelength and being delivered through an endoscopic system. The sample is imaged using a second light source, different from the first light source, having a second wavelength, different from the first wavelength and being delivered through the endoscopic system (block 3010). Receive information related to the first and second light sources from the sample at a camera (block 3020). The light at the first wavelength is configured to reflect off a surface of the sample into the camera and light at the second wavelength is configured to penetrate the sample and provide information related to the sample to the camera through the endoscopic system. The information related to the first and second light sources provided by the camera are combined at a processor to image an anatomical structure of the sample, image physiology of blood flow and perfusion of the sample and/or synthesize the anatomical structure and the physiology of blood flow and perfusion of the sample in terms of a blood flow rate distribution (block 3030). The illumination, analysis and display may be performed using the endoscopic system. The endoscopic system may be configured to communicate with a multi-spectral physiologic visualization (MSPV) operating system.

Referring now to FIG. 31, a diagram illustrating details with respect to FOV in various embodiments of the present inventive concept will be discussed. FIG. 31 illustrates a viewing circle 3100 associated with an endoscope 3103. The angular FOV ($FOV_{WS}$) is depicted in degrees. The radius r of the viewing circle 3100 is directly related to linear FOV as discussed below with respect to Eqn. 11. As illustrated in FIG. 31, the object distance d is 50 mm in the example illustrated therein.

Generally, the FOV may be specified in one of the two ways: angular FOV specified in degrees; and linear FOV ($FOV_{WS}$) specified in the lengths/ratio of the lengths. With object distance and/or working distance being defined, the angular/linear FOV can be converted to the other using, for example, Eqn. 11 discussed below. The FOV of an endoscope 3103 is measured by the cone angle $FOV_{ws}$ as shown in FIG. 21, which is the angular FOV. A cone angle $FOV_{WS}$ of a rigid endoscope can range from about 0 to about 90 degrees, typically about 30 degrees.

Example embodiments of the present inventive concept have used an Olympus 10 mm rigid laparoscope having a 75 degree FOV. By changing the working distance, the linear FOV can range from under 1.0 cm×1.0 cm to above 10.0 cm×10.0 cm according to Eqn. 11.

$$FOV_{WS} = 2\mathrm{atan}\left(\frac{r}{d}\right); \quad \text{Eqn. (11)}$$

where $FOV_{WS}$ is the angular FOV in degrees; r is the radius of the viewing circle, which is directly related to linear FOV; and d is the object distance.

By using an appropriate optical adapter lens, embodiments of the present inventive concept can be used to design a system having from 0 to 180 degree angular FOV and the corresponding linear FOV can be derived using Eqn. 11 set out above.

In the drawings and specification, there have been disclosed example embodiments of the inventive concept. Although specific terms are employed, they are used in a generic and descriptive sense only and not for purposes of limitation, the scope of the inventive concept being defined by the following claims.

That which is claimed is:

1. A multispectral imaging system, the system comprising:
   a first light source having a first wavelength configured to image a sample;
   a second light source, different from the first light source, having a second wavelength, different from the first wavelength, configured to image the sample;
   at least a third light source, different from the first and second light sources, having a third wavelength, different from the first and second wavelengths, configured to image the sample;
   a multi-sensor camera having a plurality of sensors, each of the plurality of sensors configured to receive information related to one of the first, second and at least third light sources from the sample, wherein light at the first wavelength is configured to image a surface of the sample into a first of the plurality of sensors of the multi-sensor camera; wherein light at the second wavelength is configured to penetrate the sample to a first depth and provide information related to the sample to a second of the plurality of sensors of the multi-sensor camera; and wherein light at the at least third wavelength is configured to penetrate the sample at a second depth, different from the first depth of the light at the second wavelength, and provide information related to the sample to a third of the plurality of sensors of the multi-sensor camera, the information related to the first, second and third light sources being aligned and synchronized when provided to the first, second and third sensors of the multi-sensor camera; and
   a processor configured to combine the information related to the first, second and at least third light sources provided by the multi-sensor camera to image an anatomical structure of the sample, image physiology of blood flow and perfusion of the sample and/or synthesize the anatomical structure and the physiology of blood flow and perfusion of the sample in terms of a blood flow rate distribution,
   wherein the imaging system is directed and focused on a field of view (FOV) in a region of interest of the sample using an endoscope.

2. The system of claim 1, wherein the endoscope is configured to provide the information related to the first, second and at least third light sources to the processor and is included in an endoscopic imaging system, the endoscopic imaging system comprising:
   the multi-sensor camera;
   a control unit configured to control the multi-sensor camera and process images associated therewith;
   an image management unit configured to display and manipulate the images associated with the multi-sensor camera; and
   a system interface configured to translate the information related to the first, second and at least third light source to perform within the endoscopic imaging system such that the images associated therewith are displayed and manipulated.

3. The system of claim 2, wherein the endoscopic imaging system comprises at least one of:
   a system for endoscopic surgery including at least one of laparoscopy, thorascoscopy, and cystoscopy;
   a system for minimally invasive surgical procedures using the endoscope for illumination, visualizing, and manipulation; and
   a system for robotic procedures using the endoscope for illumination, visualizing, and manipulation.

4. The system of claim 2, wherein the endoscopic imaging system is configured:
   to illuminate cavity tissues and organs during a procedure;
   to visualize cavity tissues and organs for surgical intervention; and/or
   for surgical manipulation of cavity tissues and organs for surgical intervention.

5. The system of claim 2, wherein the endoscopic imaging system is configured to illuminate the region of interest using fibers, fiber compositions, fiber arrangements, lenses, diffusers, collimators, and/or expanders.

6. The system of claim 2:
wherein the multi-sensor camera is configured to have speeds, focus, accuracy and fidelity to obtain images using the endoscopic imaging system; and
wherein the multi-sensor camera is coupled to optic fibers of the endoscope.

7. The system of claim 6, wherein the plurality of sensors of the multi-sensor camera are arranged along a continuum from an endoscope tip to a distance remote from the endoscope coupled by image capture cabling.

8. The system of claim 1, wherein the endoscope is one of a rigid endoscope, a semi-rigid endoscope or a flexible endoscope.

9. The system of claim 8, wherein the endoscope is one of a rigid endoscope having a flexible, navigable tip or a flexible endoscope having a flexible insertion tube.

10. The system of claim 1, wherein the at least third light source having the at least the third wavelength is configured to assess a defined physiologic parameter.

11. The system of claim 1, wherein the system comprises one or more of a hand-held system, a finger probe unit, a skin patch and a mobile system.

12. The system of claim 1, wherein the multispectral imaging system comprises different blood flow and perfusion measurement technologies in one system, wherein the blood flow and perfusion measurement technologies comprise one or more of laser speckle imaging (LSI), laser Doppler imaging (LDI), florescence imaging or reflectance imaging.

13. A method for multispectral imaging in a multispectral imaging system adapted for an endoscopic system, comprising:
imaging a sample using a first light source having a first wavelength and being delivered through an endoscopic system;
imaging the sample using a second light source, different from the first light source, having a second wavelength, different from the first wavelength and being delivered through the endoscopic system;
receiving information related to the first and second light sources from the sample at a multi-sensor camera having a plurality of sensors, wherein light at the first wavelength is configured to reflect off a surface of the sample into the a first of the plurality of sensors in the multi-sensor camera and light at the second wavelength is configured to penetrate the sample and provide information related to the sample to a second of the plurality of sensors in the multi-sensor camera through the endoscopic system, the light at the first and second wavelengths being aligned and synchronized when provided to the first and second sensors of the multi-sensor camera; and
combining the information related to the first and second light sources received by the multi-sensor camera using at least one processor to image an anatomical structure of the sample, image physiology of blood flow and perfusion of the sample and/or synthesize the anatomical structure and the physiology of blood flow and perfusion of the sample in terms of a blood flow rate distribution.

14. The method of claim 13:
wherein illumination, analysis and display is performed using the endoscopic system; and
wherein the endoscopic system is configured to communicate with a multi-spectral physiologic visualization (MSPV) operating system.

15. An endoscopic imaging system, comprising:
an endoscope;
a light source unit coupled to the endoscope, the light source unit providing first, second and at least a third light source,
wherein the first light source has a first wavelength configured to image a sample;
wherein the second light source, different from the first light source, has a second wavelength, different from the first wavelength, configured to image the sample; and
wherein the at least a third light source, different from the first and second light sources, has a third wavelength, different from the first and second wavelengths, configured to image the sample;
a cameral control unit coupled to the endoscope through a camera head of a multi-sensor camera having a plurality of sensors, the camera head being adapted to receive information related to the first, second and at least third light sources, wherein light at the first wavelength is configured to image a surface of the sample into a first of the plurality of sensors of the multi-sensor camera; wherein light at the second wavelength is configured to penetrate the sample to a first depth and provide information related to the sample to a second of the plurality of sensors in the multi-sensor camera; and wherein light at the third wavelength is configured to penetrate the sample to a second depth, different from the first depth, and provide information related to the sample to a third sensor of the plurality of sensors in the multi-sensor camera, the information related to the first, second and third wavelengths being aligned and synchronized when provided to the first, second and third sensors of the multi-sensor camera; and
an image processing unit coupled to endoscope configured to combine the information related to the first, second and at least third light sources provided by the camera head to image an anatomical structure of the sample, image physiology of blood flow and perfusion of the sample and/or synthesize the anatomical structure and the physiology of blood flow and perfusion of the sample in terms of a blood flow rate distribution.

16. The system of claim 15, wherein the endoscopic imaging system comprises at least one of:
a system for endoscopic surgery including at least one of laparoscopy, thorascoscopy, and cystoscopy;
a system for minimally invasive surgical procedures using the endoscope for illumination, visualizing, and manipulation; and
a system for robotic procedures using the endoscope for illumination, visualizing, and manipulation.

17. The system of claim 15, wherein the endoscopic imaging system is configured to:
illuminate cavity tissues and organs during a procedure;
visualize cavity tissues and organs for surgical intervention; and/or
surgical manipulation of cavity tissues and organs for surgical intervention.

18. The system of claim 15, wherein the endoscopic imaging system is configured to illuminate a region of interest by using fibers, fiber compositions, fiber arrangements, lenses, diffusers, collimators, and/or expanders.

19. The system of claim 15, wherein the endoscope is one of a rigid endoscope having a flexible, navigable tip and or a flexible endoscope having a flexible insertion tube.

20. The system of claim 15, further comprising an accessory unit coupled to the endoscope through any of air, water and/or open channel tubes.

* * * * *